(12) United States Patent
Steinmetz et al.

(10) Patent No.: US 11,998,594 B2
(45) Date of Patent: Jun. 4, 2024

(54) ANTI-CANCER PLANT VIRUS PARTICLES LINKED TO HER2 ANTIGENS

(71) Applicant: CASE WESTERN RESERVE UNIVERISTY, Cleveland, OH (US)

(72) Inventors: Nicole F. Steinmetz, San Diego, CA (US); Sourabh Shukla, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 900 days.

(21) Appl. No.: 17/039,312

(22) Filed: Sep. 30, 2020

(65) Prior Publication Data

US 2021/0060147 A1    Mar. 4, 2021

Related U.S. Application Data

(63) Continuation-in-part of application No. 16/883,444, filed on May 26, 2020, now abandoned, which is a continuation of application No. 16/161,596, filed on Oct. 16, 2018, now Pat. No. 10,660,949, which is a continuation of application No. 15/300,931, filed as application No. PCT/US2015/024086 on Apr. 2, 2015, now Pat. No. 10,098,936.

(60) Provisional application No. 61/974,053, filed on Apr. 2, 2014.

(51) Int. Cl.
| | |
|---|---|
| *A61K 39/00* | (2006.01) |
| *A61K 39/295* | (2006.01) |
| *A61K 39/39* | (2006.01) |
| *A61P 35/00* | (2006.01) |
| *C07K 14/005* | (2006.01) |
| *C12N 7/00* | (2006.01) |

(52) U.S. Cl.
CPC .. *A61K 39/001106* (2018.08); *A61K 39/0011* (2013.01); *C07K 14/005* (2013.01); *C12N 7/00* (2013.01); *A61K 2039/5258* (2013.01); *A61K 2039/54* (2013.01); *A61K 2039/542* (2013.01); *C12N 2770/26023* (2013.01); *C12N 2770/26043* (2013.01); *C12N 2770/26071* (2013.01)

(58) Field of Classification Search
CPC ................ A61P 35/00; A61K 39/0011; A61K 39/001106; A61K 2039/5258; A61K 2039/64
See application file for complete search history.

(56) References Cited

U.S. PATENT DOCUMENTS

| | | | |
|---|---|---|---|
| 5,004,606 A | 4/1991 | Frincke | |
| 9,925,281 B2 | 3/2018 | Steinmetz et al. | |
| 10,086,095 B2 | 10/2018 | Steinmetz et al. | |
| 10,207,014 B2 | 2/2019 | Steinmetz et al. | |
| 10,478,510 B2 | 11/2019 | Steinmetz | |
| 11,020,497 B2 | 6/2021 | Steinmetz et al. | |
| 11,167,047 B2 | 11/2021 | Steinmetz et al. | |
| 11,253,610 B2 | 2/2022 | Steinmetz | |
| 2007/0248617 A1 | 10/2007 | Bachmann et al. | |
| 2007/0258889 A1 | 11/2007 | Douglas | |
| 2007/0284545 A1 | 12/2007 | Isacsson et al. | |
| 2010/0183504 A1 | 7/2010 | Chen | |
| 2012/0195962 A1 | 8/2012 | Kammer et al. | |
| 2015/0033418 A1 | 1/2015 | Lommel et al. | |
| 2015/0265696 A1 | 9/2015 | Gourapura et al. | |
| 2020/0179468 A1 | 6/2020 | Steinmetz | |
| 2022/0211881 A1 | 7/2022 | Steinmetz | |

FOREIGN PATENT DOCUMENTS

| | | |
|---|---|---|
| JP | 2009524699 A | 7/2009 |
| WO | 01/18199 A1 | 3/2001 |
| WO | 2003092623 A2 | 11/2003 |
| WO | 2012078069 A1 | 6/2012 |
| WO | 2012155262 A1 | 11/2012 |
| WO | 2013181557 A1 | 12/2013 |
| WO | 2014059021 A1 | 4/2014 |
| WO | 2014139672 A1 | 9/2014 |
| WO | 2015/188110 A1 | 12/2015 |
| WO | 2016019393 A1 | 2/2016 |
| WO | 2016073972 A1 | 5/2016 |
| WO | 2016/149264 A1 | 9/2016 |
| WO | 2017/004123 A1 | 1/2017 |

OTHER PUBLICATIONS

Applicant: Case Western Reserve University; "Cancer Immunotherapy Using Virus Particles"; European Patent Application No. 21201960.8; Extended European Search Report dated Jan. 19, 2022; 11 pgs.
Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Gonzalez Maria Jet al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.

(Continued)

*Primary Examiner* — Barry A Chestnut
(74) *Attorney, Agent, or Firm* — TAROLLI, SUNDHEIM, COVELL & TUMMINO, LLP

(57) ABSTRACT

An anti-cancer virus composition including an icosahedral-shaped plant virus or virus-like particle linked to a HER2 antigen is described. The anti-cancer virus composition can be used for methods of treating or decreasing the risk of developing a HER2-expressing cancer in a subject by administering to a subject in need thereof an effective amount of the anti-cancer virus composition.

19 Claims, 13 Drawing Sheets

Specification includes a Sequence Listing.

(56) References Cited

OTHER PUBLICATIONS

Patrick h. lizotte: "Novel approaches to targeting innate immunity for cancer immunotherapy", Proquest Dissertations Publishing, May 2015 (May 2015), XP002780316, Retrieved from the Internet: URL:https://search.proquest.com/docview/16 95832154?pq-origsite=gscholar [retrieved on Apr. 19, 2018].

Saunders K et al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].

Applicant: Case Western Reserve University; "Cancer Immunotherapy Using Virus Particles"; European Patent Application No. 18764856.3 for Supplementary European Search Report dated Dec. 22, 2020; 8 pgs.

Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.

Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.

Nicole F.Steinmetz; "Viral Nanoparticle Multimers"; U.S. Appl. No. 14/761,444, filed Jul. 16, 2015; Final Office Action dated Mar. 11, 2021; 11 pgs.

"CWRU researcher to turn plant virus shells against human cancers", The Daily, CWRU Researcher to Turn Plant Virus Shells Against Human Cancers. Case Western Reserve University, Apr. 18, 2016.

Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.

Applicant: Case Western Reserve University; "Cancer Immunotherapy Using Virus Particles"; Canadian Office Action, dated Aug. 4, 2020; 3 pgs.

Applicant: Case Western Reserve University; "Plant Virus Particles for Delivery of Antimitotic Agents"; Extended European Search Report; dated Aug. 25, 2020; 11 pgs.

Canan Uluog, et al.: "Intermediate dose of methotrexate toxicity in non-Hodgkin lymphoma", General Pharmacology, vol. 32, 1999, pp. 215-218, XP55711259.

Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.

European Search Report for Patent Application No. 15857504.3-1111/3215520, dated May 7, 2018.

Francisco, Joseph A., et al.; "CAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.

International Search Report for Application No. PCT/US15/59675 (dated 2016).

Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.

Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.

Lizotte, et al., "Plant-derived viral-like nanoparticle immunotherapy suppress development of metastatic lung cancer", Journal of Immunology, vol. 194, Issue 1 Supplement, May 2015; 4 pgs.

Matsuura et al. Self-assembly of Ni-NT A-modified [3-annulus peptides into artificial viral capsids and encapsulation of His-tagged proteins. Org. Biomol. Chem., 2016, 14, 7869. DOI: 10.1039/c6ob01227b (Year: 2016).

Miermont et al., "Cowpea Mosaic Virus Capsid: A promising Carrier for the Development of Carbohydrate Based Antitumor Vaccines", Chem. Eur. J., 2008, vol. 14, pp. 4939-4947.

Office action for Chinese Patent Application No. 201580063662.6, dated Mar. 4, 2020.

Office action for European Patent Application No. 15 857 504.3-1111, dated Mar. 18, 2020.

Office action for Japanese Patent Application No. 2017-524349, dated Jan. 31, 2020; dated Feb. 10, 2020; 6 pgs.

Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].

Plchova et al. Expression of Human papillomavirus 16 E7ggg oncoprotein on N- and C-terminus of Potato virus X coat protein in bacterial and plant cells. Protein Expression and Purification 77 (2011); p. 146-152.

Sheen et al., "Stimulating Antitumor Immunity with Nanoparticles", Wiley Interdiscip Rev Nanomed Nanobiotechnol, Oct. 2014, vol. 6, pp. 496-505.

Smyth et al. Treatment of rapidly growing K-BALB and CT26 mouse tumours using Semliki Forest virus and its derived vector. Gene Therapy (2005) 12, 147-159.

Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.

Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.

Wen et al. Design of virus-based nanomaterials for medicine, biotechnology, and energy. Chem. Soc. Rev., 2016, 45, 4074. DOI: 10.1039/c5cs00287g (Year: 2016).

Yildiz, et al., "Applications of viral nanoparticles in medicine", Current Opinion in Biotechnology, vol. 22, Issue 6, (2011); pp. 901-908.

Lee, et al.; "PEGylation to Improve Protein Stability During Melt Processing"; Macromol Biosci 1-43, 57-75, Oct. 2015 vol. 15 No. 10 pp. 1332-1337.

Czapar, Anna et al. Tobacco Mosaic Virus Delivery of Phenanthriplatin for Cancer therapy. American Chemical Society. Nano 2016 (10) pp. 4119-4126 (Year: 2016).

Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).

Le, Duc et al. Chemical addressability of potoato virus X for its applications in bio/nanotechnology. El Sevier. Journal of Structural Biology 200 (2017). pp. 360-368. (Year: 2017).

Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).

Nicole F. Steinmetz, U.S. Appl. No. 16/998,210, filed Aug. 7, 2020; Non-Final OA dated Dec. 7, 2022.

Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).

Bruckman et al. (Nano Letters. Mar. 2014; 14: 1551-1558).

Imamura et al. ("FOXA 1 promotes tumor progression in prostate cancer via the insulin-like growth factor binding protein 3 pathway." (2012).

Lam, et al. (WIREs Nanomed Nanobiotechnol Jan./Feb. 2018 vol. 10: 1-18).

Mitoxantrone. Drug Bank Online. Website. https://go.drugbank.com/drugs/DB01204. (Accessed Dec. 15, 2022) (Year: 2022).

Mosquera et al. (Acc. Chem. Res. 2018, 51, 9, 2305-2313 Publication Date: Aug. 29, 2018.

Nicole F.Steinmetz; U.S. Appl. No. 16/597,509, filed Oct. 9, 2019; Non-Final Office Action, dated Dec. 27, 2022; 12 pgs.

Nicole F.Steinmetz; U.S. Appl. No. 16/759,652, filed Apr. 27, 2020; Final Office Action, dated Dec. 12, 2022; 15 pgs.

(56) References Cited

OTHER PUBLICATIONS

Nicole F.Steinmetz; U.S. Appl. No. 17/129,463, filed Dec. 21, 2020; Non-Final Office Action, dated Dec. 8, 2022; 32 pgs.
Nicole F.Steinmetz; U.S. Appl. No. 17/522,182, filed Nov. 9, 2021; Non-Final Office Action, dated Jan. 5, 2023; 27 pgs.
Nicole F.Steinmetz; U.S. Appl. No. 17/677,147, filed Feb. 22, 2022; Non-Final Office Action, dated Jan. 13, 2023; 22 pgs.
Pellico et al. (Contrast Media and Molecular Imaging. 2019; Article ID 1845637: 1-13).
Pretto et al. ("Versatile reversible cross-linking strategy to stabilize CCMV virus like particles for efficient siRNA delivery." Bioconjugate chemistry 30.12 (2019): 3069-3077).
Royston et al. (Journal of Colloidal and Interface Science. 2009; 332: 402-407).
Tamoxifen. Drug Bank Online. Website. https://go.drugbank.com/drugs/DB00675. (Accessed: Dec. 15, 2022) (Year: 2022).
Temming et al. (bioconjugate Chemistry. 2006; 17: 1385-1394).
Xiao et al. (International Journal of Molecular Medicine. 2016; 38: 1319-326).
Zhang et al. (Theranostics. 2018; 8 (9): 2521-2548).
Applicant: Case Western Reserve University; "Cancer Immunotherapy Using Virus Particles"; Office Action, dated Aug. 4, 2020; 3 pgs.
Applicant: Case Western Reserve University; "Plant Virus Particles for Delivery of Antimitotic Agents"; Extended European Search Report; dated Aug. 17, 2020; 11 pgs.
PCT International Search Report and Written Opinion for PCT/US2015/024086, dated Jul. 13, 2015, pp. 1-9.
Jasinska, Joanna, et al. "Inhibition of tumor cell growth by antibodies induced after vaccination with peptides derived ram the extracellular domain of Her-2/neu." International journal of cancer 107.6 (2003): 976-983.
Oyston, et al., "The current challenges for vaccine development", Journal of Medical Microbiology (2012), 61, pp. 889-894.
Steinmetz, et al., "Potato Virus X as a Novel Platform for Potential Biomedical Applications", American Chemical Society, 2010, pp. 305-312.

CH401ᵣ : YQDMVLWKDVFRKNNQLAP
CH401ₕ : YQDTKWKDFHKNNQLALT

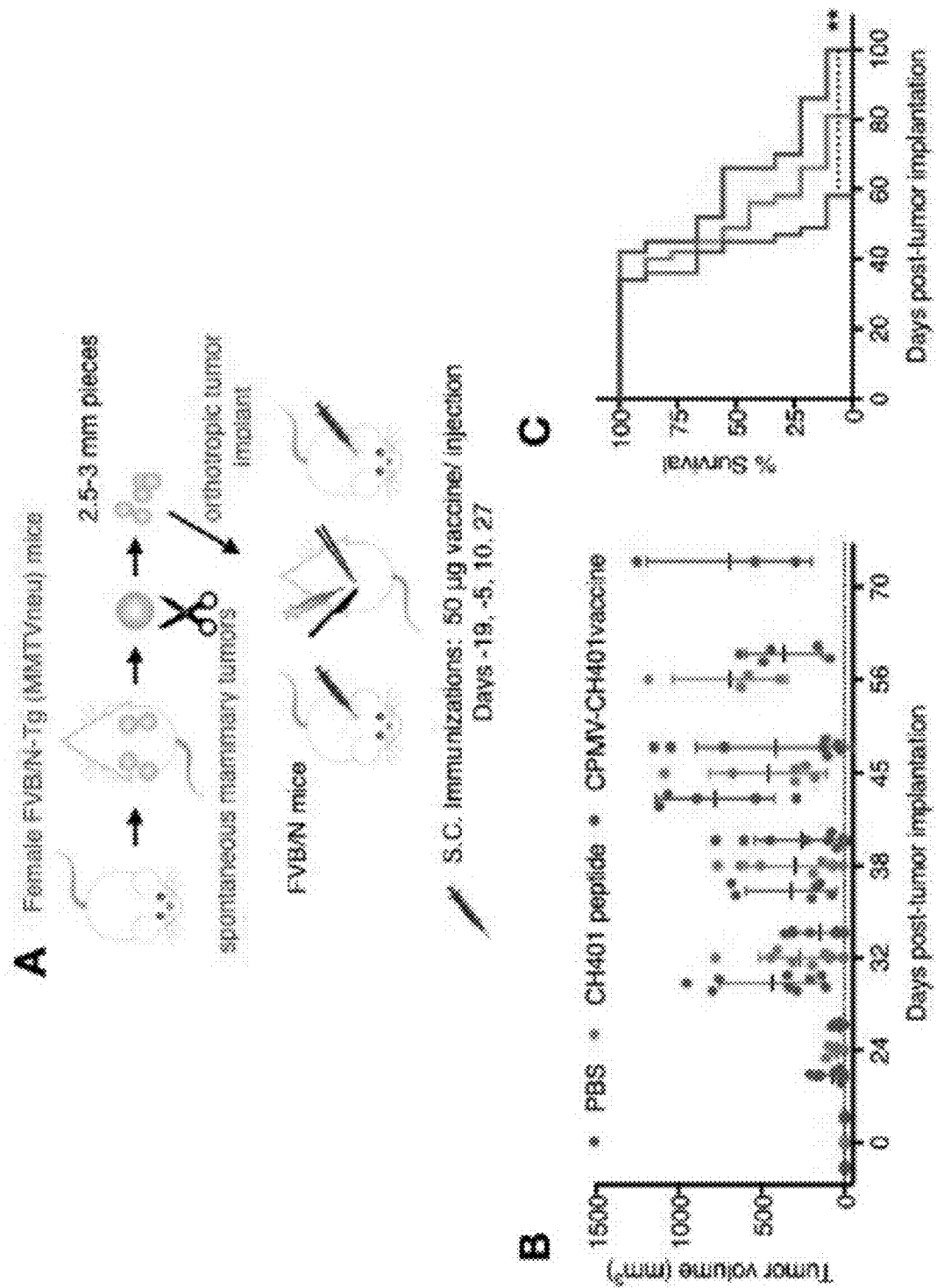
Figs. 3A-C

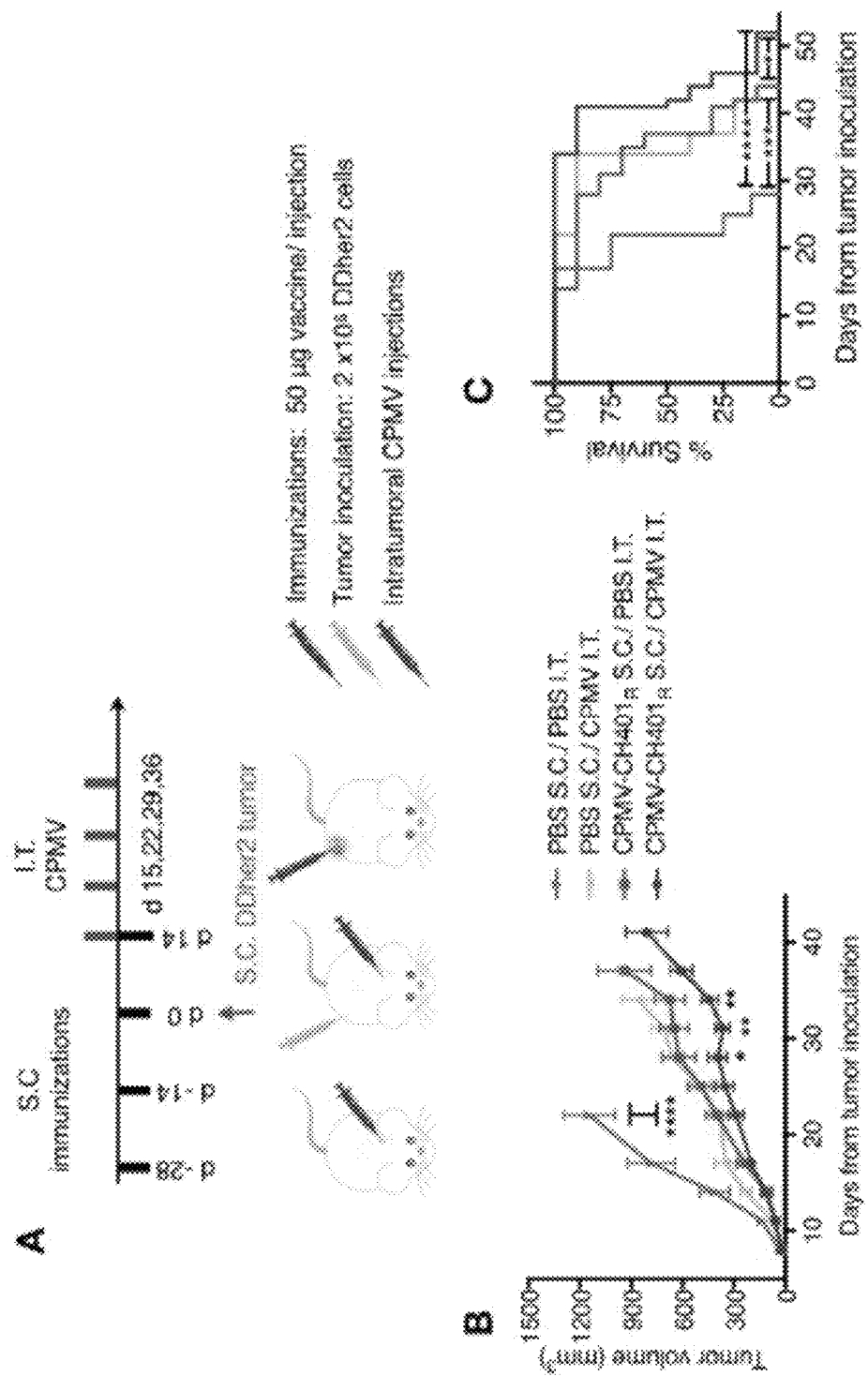
Figs. 5A-C

SEQUENCE LISTING

<160> NUMBER OF SEQ ID NOS: 16

<210> SEQ ID NO 1
<211> LENGTH: 21
<212> TYPE: PRT
<213> ORGANISM: Homo sapiens

<400> SEQUENCE: 1

Pro Glu Ser Phe Asp Gly Asp Pro Ala Ser Asn Thr Ala Pro Leu Gln
1               5                   10                  15

Pro Glu Gln Leu Gln
            20

<210> SEQ ID NO 2
<211> LENGTH: 21
<212> TYPE: PRT
<213> ORGANISM: Artificial Sequence
<220> FEATURE:
<223> OTHER INFORMATION: P4 HER2 antigen including glycine and cysteine
      linker

<400> SEQUENCE: 2

Pro Glu Ser Phe Asp Gly Asp Pro Ala Ser Asn Thr Ala Pro Leu Gln
1               5                   10                  15

Pro Gly Gly Gly Cys
            20

<210> SEQ ID NO 3
<211> LENGTH: 24
<212> TYPE: PRT
<213> ORGANISM: Homo sapiens

<400> SEQUENCE: 3

Pro Leu His Asn Gln Glu Val Thr Ala Glu Asp Gly Thr Gln Arg Ala
1               5                   10                  15

Glu Lys Cys Ser Lys Pro Cys Ala
            20

<210> SEQ ID NO 4
<211> LENGTH: 19
<212> TYPE: PRT
<213> ORGANISM: Homo sapiens

<400> SEQUENCE: 4

Leu Phe Arg Asn Pro His Gln Ala Leu Leu His Thr Ala Asn Arg Pro
1               5                   10                  15

Glu Asp Glu

<210> SEQ ID NO 5
<211> LENGTH: 18
<212> TYPE: PRT
<213> ORGANISM: Homo sapiens

<400> SEQUENCE: 5

Lys Pro Asp Leu Ser Tyr Met Pro Ile Trp Lys Phe Pro Asp Glu Glu
1               5                   10                  15

Gly Ala

<210> SEQ ID NO 6
<211> LENGTH: 20
<212> TYPE: PRT
<213> ORGANISM: Homo sapiens

-continued

<400> SEQUENCE: 6

Ile Asn Gly Thr His Ser Cys Val Asp Leu Asp Asp Lys Gly Cys Pro
1               5                   10                  15

Ala Glu Gln Arg
            20

<210> SEQ ID NO 7
<211> LENGTH: 17
<212> TYPE: PRT
<213> ORGANISM: Homo sapiens

<400> SEQUENCE: 7

Cys Arg Val Leu Gln Gly Leu Pro Arg Glu Tyr Val Asn Ala Arg His
1               5                   10                  15

Cys

<210> SEQ ID NO 8
<211> LENGTH: 14
<212> TYPE: PRT
<213> ORGANISM: Homo sapiens

<400> SEQUENCE: 8

Tyr Met Pro Ile Trp Lys Phe Pro Asp Glu Glu Gly Ala Cys
1               5                   10

<210> SEQ ID NO 9
<211> LENGTH: 18
<212> TYPE: PRT
<213> ORGANISM: Homo sapiens

<400> SEQUENCE: 9

Tyr Gln Asp Thr Ile Leu Trp Lys Asp Ile Phe His Lys Asn Asn Gln
1               5                   10                  15

Leu Ala

<210> SEQ ID NO 10
<211> LENGTH: 46
<212> TYPE: PRT
<213> ORGANISM: Homo sapiens

<400> SEQUENCE: 10

Lys Leu Leu Ser Leu Ile Lys Gly Val Ile Val His Arg Leu Glu Gly
1               5                   10                  15

Val Glu Gly Pro Ser Leu Cys Pro Ile Asn Cys Thr His Ser Cys Val
                20                  25                  30

Asp Leu Asp Asp Lys Gly Cys Pro Ala Glu Gln Arg Ala Ser
            35                  40                  45

<210> SEQ ID NO 11
<211> LENGTH: 36
<212> TYPE: PRT
<213> ORGANISM: Homo sapiens

<400> SEQUENCE: 11

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
                20                  25                  30

Phe Cys Val Ala
            35

```
<210> SEQ ID NO 12
<211> LENGTH: 30
<212> TYPE: PRT
<213> ORGANISM: Homo sapiens

<400> SEQUENCE: 12

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
            20                  25                  30

<210> SEQ ID NO 13
<211> LENGTH: 20
<212> TYPE: PRT
<213> ORGANISM: Homo sapiens

<400> SEQUENCE: 13

Tyr Gln Asp Thr Ile Leu Trp Lys Asp Ile Phe His Lys Asn Asn Gln
1               5                   10                  15

Leu Ala Leu Thr
            20

<210> SEQ ID NO 14
<211> LENGTH: 20
<212> TYPE: PRT
<213> ORGANISM: Homo sapiens

<400> SEQUENCE: 14

Tyr Gln Asp Met Val Leu Trp Lys Asp Val Phe Arg Lys Asn Asn Gln
1               5                   10                  15

Leu Ala Pro Val
            20

<210> SEQ ID NO 15
<211> LENGTH: 25
<212> TYPE: PRT
<213> ORGANISM: Homo sapiens

<400> SEQUENCE: 15

Tyr Gln Asp Thr Ile Leu Trp Lys Asp Ile Phe His Lys Asn Asn Gln
1               5                   10                  15

Leu Ala Leu Thr Gly Pro Ser Leu Cys
            20                  25

<210> SEQ ID NO 16
<211> LENGTH: 25
<212> TYPE: PRT
<213> ORGANISM: Homo sapiens

<400> SEQUENCE: 16

Tyr Gln Asp Met Val Leu Trp Lys Asp Val Phe Arg Lys Asn Asn Gln
1               5                   10                  15

Leu Ala Pro Val Gly Pro Ser Leu Cys
            20                  25
```

ANTI-CANCER PLANT VIRUS PARTICLES LINKED TO HER2 ANTIGENS

RELATED APPLICATION

This application is a Continuation-in-part of patent application Ser. No. 16/883,444, filed May 26, 2020, which is a Continuation of U.S. Ser. No. 16/161,596, filed Oct. 16, 2018 (Now U.S. Pat. No. 10,660,949), which is a Continuation of U.S. Ser. No. 15/300,931, filed Sep. 30, 2016 (Now U.S. Pat. No. 10,098,936), which is a National Stage Entry of PCT/US2015/024086, filed Apr. 2, 2015, which claims priority from U.S. Provisional Application No. 61/974,053 filed Apr. 2, 2014, the subject matter of which are incorporated herein by reference in their entirety.

BACKGROUND

Approximately 200,000 women will be diagnosed with breast cancer this year and more than 40,000 of those will die from the disease. About 25-30% of breast cancer patients overexpress the human epidermal growth factor receptor 2 (HER2/neu/ErbB2). HER2 has been associated with aggressive tumors having rapid progression to death, poor prognosis and short disease free survival, high rate of metastasis, high risk of relapse/recurrence, resistance to chemotherapy or hormone replacement therapies. Ross J S, Fletcher J A, The Oncologist; 3:237-52 (1998). While widely used in the clinic, HER2 targeting therapeutic antibodies are associated with cardiac toxicity and congestive heart failure, in particular their combination with chemotherapy regimens leads to significant untoward effects. Limited patient sensitivity and development of early resistance to these monoclonal antibodies further limits the benefits of this approach.

Trastuzumab (Herceptin) is a humanized monoclonal antibody that binds HER2 with high affinity. Passive immunotherapy with trastuzumab has dramatically improved outcomes for HER2-positive breast cancer patients. Dawood et al., J Clin Oncol.; 28:92-8A (2010). A limitation of immunotherapy with trastuzumab is the short half-life requiring frequent administration. Furthermore, passive immunotherapy with trastuzumab does not protect patients from development of metastasis or recurrence. To overcome the challenges of passive immunotherapy, cancer vaccines are under development and clinical testing. Disis et al., Immunology, 93:192-9 (1998); Nanda N K, Sercarz E E, Cell, 82:13-7 (1995).

HER2 cancer vaccines have several advantages compared to passive immunotherapy. Ladjemi et al., Cancer immunology, immunotherapy:CII, 59:1295-312 (2010). Establishment of a memory immune response could overcome resistance to passive immunotherapies upon repeated usage. A cancer vaccine holds the promise to prevent recurrence of the disease or progression to metastatic disease. Administration of a prophylactic vaccine (in high risk groups) has the potential to prevent the development of the disease before doctors would be able to diagnose its onset. Lastly, cancer vaccines offer practical advantages such as lower costs based on a less intensive treatment schedule.

Many different strategies have been proposed to overcome self-tolerance associated with the HER2 self-antigen, including depletion of regulatory T cells (Weiss et al., PLoS One. 2012;7:e31962), altering the natural antigen to enhance immunogenicity, or presenting antigenic HER2 epitopes to the host in an altered molecular environment (foreign to the host). Disis et al., Journal of immunology, 156:3151-8 (1996). Approaches include vaccines based on proteins, peptides (Ladjemi et al., Cancer immunology, immunotherapy:CII. 2010; 59:1295-312), DNA (Radkevich-Brown et al., Cancer research. 2009;69:212-8), anti-idiotype antibodies (de Cerio et al., Oncogene. 2007; 26:3594-602), autologous cells, dendritic cells (Saha A, Chatterjee SK., Cellular immunology. 2010; 263:9-21), and tumor cells. Dols et al., Journal of immunotherapy. 2003;26:163-70.

Peptide-based vaccines constitute the largest group of cancer vaccines under preclinical and clinical evaluation. Several HER2 peptides derived from the extracellular domain (Mittendorf et al., Cancer immunology, immunotherapy:CII. 2008; 57:1511-21), transmembrane domain (Mittendorf et al., Cancer. 2006; 106:2309-17) or intracellular domains (Disis et al., Journal of clinical oncology, 2004;22:1916-25) are in clinical trials as single-epitope or in combinations as multi-epitope vaccines. Several approaches have been shown to generate a HER2-specific response mediated by CTLs (cellular immunity) and/or humoral immunity. Dakappagari et al., Journal of immunology. 2003; 170:4242-53; Jasinska et al., Int J Cancer. 2003; 107:976-83. Nevertheless, peptide-based vaccines suffer from weak and short-lived immunogenicity and are dependent on adjuvants. In the absence of suitable adjuvants the peptides are prone to proteolytic degradation resulting in shorter circulation times. Thus, there is a need for improved vectors and epitope presentation strategies to develop stable peptide-based vaccines.

Plant virus-based vectors displaying antigenic peptides fused to the coat proteins can be readily purified, and presentation of multiple copies of antigen on a macromolecular assembly can significantly enhance the immunogenicity of these epitopes. Jegerlehner et al., Vaccine, 20:3104-12 (2002). Several chimeric platforms have been shown to elicit protective immunity in diverse hosts in preclinical settings. Canizares et al., Immunology and cell biology, 83:263-70 (2005). A broad range of plant virus-like particles (VLPs) have been established, such as those based on Cowpea mosaic virus (CPMV), Cowpea chlorotic mottle virus (CCMV), Brome mosaic virus (BMV), Potato virus X (PVX) and Tobacco mosaic virus (TMV).

Each cancer type is unique but many solid tumors metastasize throughout the body. An option for targeted such tumors is direct application of immunostimulatory reagents into the suspected metastatic site or tumor environment (e.g., proximal a tumor site) or even directly into an identified tumor (i.e., intratumoral injection). This approach, in situ vaccination, can modulate the local microenvironment and, like therapies such as T cell checkpoint blocking antibodies, can relieve immunosuppression and potentiate anti-tumor immunity against antigens expressed by the tumor. Recent studies have demonstrated that VLP therapeutic efficacy extends beyond the specific antigen array that they carry and that they may possess inherent immunogenic properties that can stimulate immune responses against infectious agents that do not carry any antigen included in the VLP. Rynda-Apple et al., Nanomed., 9(12):1857-68 (2014)).

SUMMARY

Embodiments described herein relate to anti-cancer plant virus particles and their use in the treatment of cancer. The anti-cancer plant virus particle includes an icosahedral-shaped plant virus or plant virus-like particle linked to an HER2 antigen. The HER2 antigen can be conjugated to the external surface of the icosahedral-shaped plant virus or plant virus-like particle. In some embodiments, about 30

HER2 antigens are conjugated to the external surface of the icosahedral-shaped plant virus or plant virus-like particle. The anti-cancer virus particle can further include a pharmaceutically acceptable carrier and/or an adjuvant.

In some embodiments, the icosahedral-shaped plant virus or plant virus-like particle is of the Secoaviridae family. In some embodiments, the icosahedral-shaped plant virus or plant virus-like particle is of the genus *Comovirus*, such as a cowpea mosaic virus (CPMV) or CPMV virus-like particle.

In some embodiments, the HER2 antigen includes a B-cell and a T-cell epitope from the extracellular domain of the HER2 protein. In some embodiments, the HER2 antigen includes all or a portion of the amino acid sequence located between position 163 and 182 of human HER2 protein. In some embodiments, the HER2 antigen includes a peptide having an amino acid sequence selected from YQDTILWKDIFHKNNQLALT (SEQ ID NO:13) and YQDMVLWKDVFRKNNQLAPV (SEQ ID NO:14). In an exemplary embodiment, the HER2 antigen includes a peptide having the amino acid sequence YQDTILWKDIFHKNNQLALT (SEQ ID NO:13). In some embodiments, the HER2 antigen includes a cysteine terminated HER2 antigen with an intervening flexible linker, such as a peptide having the amino acid sequence selected from YQDTILWKDIFHKNNQLALT-GPSL-C (SEQ ID NO:15) and YQDMVLWKDVFRKNNQLAPV-GPSL-C (SEQ ID NO:16).

Additional embodiments herein relate to methods of treating or decreasing the risk of developing a HER2-expressing cancer in a subject. The method includes administering to a subject in need thereof an effective amount of the anti-cancer plant virus composition including an icosahedral-shaped plant virus or virus-like particle linked to a HER2 antigen. The HER2 antigen can be conjugated to the external surface of the plant virus or plant virus-like particle. In some embodiments, about 30 HER2 antigens are conjugated to the external surface of the icosahedral-shaped plant virus or plant virus-like particle. The anti-cancer virus particle can further include a pharmaceutically acceptable carrier. In some embodiments, the therapeutically effective amount of the anti-cancer composition administered to the subject for the treatment of cancer is the amount effective to enhance uptake and activation of antigen presenting cells and promote B-cell and T-helper cell immune response in the subject.

In some embodiments, the icosahedral-shaped plant virus or plant virus-like particle is of the Secoaviridae family. In some embodiments, the icosahedral-shaped plant virus or plant virus-like particle is of the genus *Comovirus*, such as a cowpea mosaic virus (CPMV) or CPMV virus-like particle.

In some embodiments, the HER2 antigen includes a B-cell and a T-cell epitope from the extracellular domain of the HER2 protein. In some embodiments, the HER2 antigen includes a HER2 B-cell and a T-cell epitope homologous to the species of subject being treated. In some embodiments, the HER2 antigen includes all or a portion of the amino acid sequence located between position 163 and 182 of human HER2 protein. In some embodiments, the HER2 antigen includes a peptide having an amino acid sequence selected from YQDTILWKDIFHKNNQLALT (SEQ ID NO:13) and YQDMVLWKDVFRKNNQLAPV (SEQ ID NO:14). In an exemplary embodiment, the HER2 antigen includes a peptide having the amino acid sequence YQDTILWKDIFHKNNQLALT (SEQ ID NO:13). In some embodiments, the HER2 antigen includes a cysteine terminated HER2 peptide antigen with an intervening flexible linker, such as a peptide having the amino acid sequence selected from

```
                                      (SEQ ID NO: 15)
YQDTILWKDIFHKNNQLALT-GPSL-C
and
                                      (SEQ ID NO: 16)
YQDMVLWKDVFRKNNQLAPV-GPSL-C.
```

In some embodiments, the HER2-expressing cancer is selected from a breast, ovary, recto-colon, lung, prostate, stomach, pancreatic, and biliary cancer. In some embodiments, the HER2-expressing cancer is a HER2+ breast cancer. Anti-cancer plant virus compositions described herein can be administered parenterally. In some embodiments, the anti-cancer composition is administered subcutaneously.

In some embodiments, the method of treating or decreasing the risk of developing a HER2-expressing cancer in a subject can further include administering a therapeutically effective amount an additional anticancer agent or therapy to the subject. In some embodiments, the additional anticancer agent is an antitumor agent, ablation and/or radiation therapy. In some embodiments, the method further includes administering an adjuvant to the subject.

Other embodiments herein relate to a method of treating or decreasing the risk of developing a HER2-expressing cancer in a subject that includes administering to a subject in need thereof an effective amount of the anti-cancer plant virus composition including an icosahedral-shaped plant virus or virus-like particle linked to a HER2 antigen in combination with the direct administration to the cancer of the subject a therapeutically effective amount of an icosahedral-shaped plant virus or plant virus-like particle, such as CPMV or empty CPMV (eCPMV). The HER2 antigen can be conjugated to the external surface of the plant virus or plant virus-like particle. In some embodiments, about 30 HER2 antigens are conjugated to the external surface of the icosahedral-shaped plant virus or plant virus-like particle. The anti-cancer virus particle can further include a pharmaceutically acceptable carrier. In some embodiments, the therapeutically effective amount of the anti-cancer composition administered to the subject for the treatment of cancer is the amount effective to enhance uptake and activation of antigen presenting cells and promote B-cell and T-helper cell immune response in the subject.

In some embodiments, the icosahedral-shaped plant virus or plant virus-like particle is of the Secoaviridae family. In some embodiments, the icosahedral-shaped plant virus or plant virus-like particle is of the genus *Comovirus*, such as a cowpea mosaic virus (CPMV) or CPMV virus-like particle.

In some embodiments, the HER2 antigen includes a B-cell and a T-cell epitope from the extracellular domain of the HER2 protein. In some embodiments, the HER2 antigen includes a HER2 B-cell and a T-cell epitope homologous to the species of subject being treated. In some embodiments, the HER2 antigen includes all or a portion of the amino acid sequence located between position 163 and 182 of human HER2 protein. In some embodiments, the HER2 antigen includes a peptide having an amino acid sequence selected from YQDTILWKDIFHKNNQLALT (SEQ ID NO:13) and YQDMVLWKDVFRKNNQLAPV (SEQ ID NO:14). In an exemplary embodiment, the HER2 antigen includes a peptide having the amino acid sequence YQDTILWKDIFHKNNQLALT (SEQ ID NO:13). In some embodiments, the HER2 antigen includes a cysteine terminated HER2 antigen with an intervening flexible linker, such as a peptide having the amino acid sequence selected from

```
                                            (SEQ ID NO: 15)
YQDTILWKDIFHKNNQLALT-GPSL-C
and (SEQ ID NO: 16)
YQDMVLWKDVFRKNNQLAPV-GPSL-C.
```

In some embodiments, the HER2-expressing cancer is selected from a breast, ovary, recto-colon, lung, prostate, stomach, pancreatic, and biliary cancer. In some embodiments, the HER2-expressing cancer is a metastatic HER2+ breast cancer. Anti-cancer plant virus compositions described herein can be administered parenterally. In some embodiments, the anti-cancer composition is administered subcutaneously. In some embodiments, the icosahedral-shaped plant virus or plant virus-like particle, such as CPMV, is administered intratumorally.

BRIEF DESCRIPTION OF THE DRAWINGS

FIGS. 3(A-C) are graphical illustrations and images showing the evaluation of CPMV-CH401 vaccine in a tumor transplant model: A) FVB/N female mice (n=10) were immunized bi-weekly with four doses of vaccine or free peptide before and after tumor implantation. Tumors harvested from female FVB/N-Tg (MMTVneu) mice were chopped into small pieces and were transplanted into the mammary fat pads of immunized and control FVB/N females and tumor growth monitored. B) Comparative tumor volumes on multiple days (to n≥3) revealed the vaccine consistently slowed tumor progression compared to peptide immunized and control mice. Statistical analysis between the tumor volumes on individual days was performed using student t-test (**p<0.005, *p<0.05). C) Kaplan-Meier plot comparing the survival benefits offered by the vaccine over control mice. Statistical analysis on the survival curves was performed using Log-rank(Mantel-Cox) test (**p<0.01).

FIGS. 5(A-C) are graphical illustrations showing Combining CPMV-CH401 vaccine with in situ vaccination with CPMV. A) A combinatorial approach was tested where CPMV-CH401 immunized mice (n=10) grafted with subcutaneous DDHER2 tumors were also treated with four weekly doses of intratumoral CPMV injections. B) Tumor growth was monitored between control untreated mice (n=8) and mice receiving CPMV-CH401 immunizations (n=10), CPMV in situ vaccination (n=10), or a combination of both (n=10). Tumor volumes were plotted to days where n≥5. Statistical analysis was performed by ordinary one-way ANOVA using Tukey's multiple comparison tests (**p<0.0001, p<0.001, *p<0.01). C) Kaplan-Meier plot compares the survival benefits offered by combination therapy over monotherapy and no treatment. Statistical analysis on the survival curves was performed using Log-rank (Mantel-Cox) test (**p<0.0001; *p<0.001, *p<0.05).

DETAILED DESCRIPTION

Figure 1D:
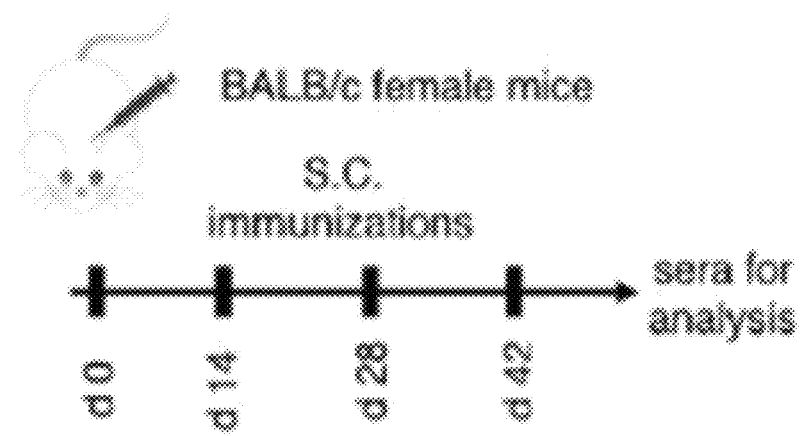
FIGS. 1(A-I) are graphical illustrations and images showing Synthesis and characterization of CPMV-CH401 vaccine and measure of immunogenicity. A) CH401 peptide (rat or human) designed with a flexible GPSL linker and a terminal cysteine residue was conjugated to lysine residues of CPMV capsid via a hetero bi-functional N-hydroxysuccinimide-PEG4-maleimide (SM-PEG4) linker using a two-step process resulting in a multivalent vaccine. B) TEM imaging shows intact CPMV-CH401 particles post purification; the scale bar is 50 nm. C) SDS gel electrophoresis was used to confirm and quantify CH401 peptide conjugation on CPMV capsid consisting of small coat proteins (S-CP, 24 kDa) and large coat protein (L-CP, 42 kDa). The modified coat proteins are indicated as S-CP-CH401 and L-CP-CH401. D) Immunization schedule used for female Balb/c mice; sera were collected before and after immunization; vaccine variants CPMV-CH401H containing the human CH401 peptide (blue) (n =9) and its rat homologue CPMV-CH401R (red) (n=10) were tested along with soluble CH401H (n=10) and soluble CH401R (n=10). E) ELISAs were performed using pooled sera (at 1:100 dilutions) in triplicates, to determine rat CH401-specific antibody titers generated by CPMV-CH401 formulations versus free peptides. F) Anti-HER2 IgG isotypes were compared between the pooled sera (at 1:100 dilutions) of CPMV-CH401R (red bars) versus CPMV-CH401H (blue bars) using ELISAs on a recombinant HER2 coated plate (in triplicates). G,H) Confocal microscopy and flow cytometry (each sample tested in triplicates) was used to confirm the binding of the pooled sera from the mice immunized with vaccine formulations to DDHER2 cells. The scale bar in G is 18 μm. Flow cytometry was analyzed using one-way ANOVA, **p<0.0001. I) MTT assays were used to compare complement-mediated cytotoxicity (CDC) of sera from immunized mice versus naive mouse sera versus anti-HER2 antibody on DDHER2 cells (4 replicates per sample). Statistical analysis between various groups performed by two-way ANOVA using Tukey's multiple comparison (p<0.0001, *p<0.001, **p<0.01, *p<0.05, and ns=no significance).

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "nanoparticle" refers to any particle having a diameter of less than 1000 nanometers (nm). In general, the nanoparticles should have dimensions small enough to allow their uptake by eukaryotic cells. Typically, the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

The phrases "parenteral administration" and "administered parenterally" are art-recognized terms and include modes of administration other than enteral and topical administration, such as injections, and include, without limitation, intratumoral, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., tumor site), such that it enters the animal's system and, thus, is subject to metabolism and other like processes, for example, subcutaneous administration.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a sufficient amount of the composition used in the practice of the invention that is effective to provide effective treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "therapeutic" treatment is a treatment administered to a subject who exhibits signs of pathology of a disease or disorder for the purpose of diminishing or eliminating those signs.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder, for example decreasing the risk of developing pathology associated with a NY-ESO-1-expressing cancer. In some embodiments, use of an anti-cancer particle described herein in a preventive treatment provides immunoprotection.

The term "adjuvant" as used herein, refers to an agent that augments, stimulates, potentiates and/or modulates an immune response in an animal. An adjuvant may or may not have an effect on the immune response in itself. Examples of adjuvants include complete Freund's adjuvant (CFA), muramyl dipeptide, Gerbu, and monophosphoryl lipid A.

The terms "immunogen", "antigen" and "antigenic peptide (epitope)" as used herein refer to a portion or portions of molecules, which are capable of inducing a specific immune response in a subject alone or in combination with an adjuvant. An epitope generally represents a portion of an antigen.

The term "immune response", as used herein, refers to an alteration in the reactivity of the immune system of an animal in response to an antigen or antigenic material and may involve antibody production, induction of cell-mediated immunity, complement activation, development of immunological tolerance, or a combination thereof.

The term "immunoprotection" as used herein, mean an immune response that is directed against one or more antigen so as to protect against disease and/or infection by a pathogen in a vaccinated animal. For purposes of the present invention, protection against disease includes not only the absolute prevention of the disease, but also any detectable reduction in the degree or rate of disease, or any detectable reduction in the severity of the disease or any symptom in the vaccinated animal as compared to an unvaccinated infected or diseased animal. Immunoprotection can be the result of one or more mechanisms, including humoral and/or cellular immunity.

The term "vaccine", as used herein, refers to a material capable of producing an immune response after being administered to a subject.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to plant virus-based human epidermal growth factor receptor 2 (HER2) anti-cancer particles and their use as adjuvant immunotherapies that can stimulate the immune system in a subject to recognize tumor-associated antigens. The anti-cancer particles can be used for methods of treating or decreasing the risk of developing an HER2 overexpressing cancer in a subject by administering to a subject in need thereof a therapeutically effective amount of the anti-cancer particles.

The anti-cancer particles include an icosahedral plant virus or virus-like particle (VLP) linked to a HER2 antigen. For example, the HER2 antigen can be conjugated to the exterior surface of the icosahedral plant virus particle. Using several mouse models of HER2+ tumors it was shown that icosahedral-shaped plant virus-based HER2 anti-cancer particles can overcome HER2 self-tolerance by activating a potent anti-HER2 immune response that delays progression of primary tumors as well as preventing metastatic spread, thereby prolonging survival in mice. It is believed the icosahedral-shaped plant virus particles facilitate efficient delivery of HER2 antigens to antigen presenting cells (APCs) in the subject to promote immune system stimulus and the processing and presentation of the antigens. It was further shown that the anti-cancer particles are capable of recognizing HER2 expressing tumor cells and instigate HER2-specific antibody production as well as effector and memory T cells, which contributes to the effectiveness of the anti-cancer particles. Thus, it is contemplated that icosahedral-shaped plant virus-based HER2 anti-cancer particles can prime an effective anti-HER2 B-cell and T-cell immune response that delays tumor progression of primary tumors as well as prevents metastatic spread and improve survival of a subject with HER2 associated cancer.

The icosahedral-shaped plant virus particles or plant virus-like particle can be nonreplicating and noninfectious in the subject to avoid infection of the subject and can be regarded as safe from a human health and agricultural perspective. In planta production prevents endotoxin contamination that may be a byproduct of other virus or virus-like particle systems derived from E. coli. The icosahedral-shaped plant virus particles or VLPs are scalable, stable over a range of temperatures (4-60° C.) and solvent:

buffer mixtures. For example, CPMV can be propogated in and purified from *Vigna unguiculata* plansts with yields of 50-100 mg virus/100 g of infected leaves.

In some embodiments, icosahedral-shaped plant virus particles or plant virus-like particles in which the viral nucleic acid is not present are linked to a HER2 antigen. Virus-like particles lacking their nucleic acid are non-replicating and non-infectious regardless of the subject into which they are introduced.

In other embodiments, the icosahedral-shaped plant virus particles include a nucleic acid within the virus particle. If present, the nucleic acid will typically be the nucleic acid encoding the virus. However, in some embodiments the viral nucleic acid may have been replaced with exogenous nucleic acid. In some embodiments, the nucleic acid is RNA, while in other embodiments the nucleic acid is DNA. A virus particle including nucleic acid will still be nonreplicating and noninfectious when it is introduced into a subject, which it cannot infect. For example, icosahedral-shaped plant virus particles will typically be nonreplicating and noninfectious when introduced into an animal subject.

An icosahedral-shaped plant virus is a virus that primarily infects plants, is non-enveloped and has capsid proteins that can self-assemble into well- organized icosahedral three-dimensional (3D) nanoscale multivalent architectures with high monodispersity and structural symmetry. Icosahedral-shaped plant viruses also include an exterior surface and interfaces between coat protein (CP) subunits that can be manipulated to allow for controlled self-assembly and multivalent ligand display of nanoparticles or molecules for varied applications.

In some embodiments, the icosahedral plant virus is a plant picornavirus. A plant picornavirus is a virus belonging to the family Secoaviridae, which together with mammalian picornaviruses belong to the order of the Picornavirales. Plant picornaviruses are relatively small (diameter of about 30nm), non-enveloped, positive-stranded RNA viruses with an icosahedral capsid. Plant picornaviruses have a number of additional properties that distinguish them from other picornaviruses, and are categorized as a subfamily of Secoviridae. In some embodiments, the icosahedral-shaped plant virus particles are selected from the Comovirinae virus subfamily. Exemplary Comovirinae subfamily viruses for use in a composition or therapeutic method described herein can include Cowpea mosaic virus (CPMV), Broad bean wilt virus 1, and Tobacco ringspot virus. In certain embodiments, the plant virus or plant virus-like particles are from the genus *Comovirus*. A preferred example of a *Comovirus* is the CPMV or CPMV-like virus particles. The immune stimulating ability of CPMV is derived from its highly organized 3D protein architecture with its encapsulated nucleic acid and an intrinsic immune cell tropism. In some embodiments, the plant virus-like particle is an empty cowpea mosaic virus-like particle (eCPMV).

Anti-cancer particle compositions of the present invention also include an HER2 antigen. In some embodiments, HER2 antigens are derived from a portion of the HER2/neu protein (also referred to herein as the HER2 protein) which are recognized by the immune system; e.g., by antibody binding. The HER2/neu proto-oncogene is expressed in breast cancer and other human cancers, and encodes a tyrosine kinase with homology to epidermal growth factor receptor. HER2/neu protein is a receptor-like transmembrane protein comprising a large cysteine-rich extracellular domain that functions in ligand binding, a short transmembrane domain, and a small cytoplasmic domain. HER2/neu is amplified and expressed in many human cancers, largely adenocarcinomas of breast, ovary, colon, and lung. In breast cancer, HER2/neu over-expression is associated with aggressive disease and is an independent predictor of poor prognosis. The HER2 protein is intimately associated with the malignant phenotype and with the aggressiveness of the malignancy, especially in breast and ovarian carcinomas. An advantage of presenting the HER2 antigen linked to an icosahedral-shaped plant virus particle is that such linked particles are capable of stimulating an immune response without having to be co-administered with an adjuvant.

The present invention includes use of any HER2 antigen capable of eliciting an immune response. Examples of HER2 antigens are described in US Patent Publication 2015/0071927, U.S. Pat. No. 7,446,185, Jasinska et al., Int. J. Cancer 107, 976-983 (2003), and Wagner et al., Breast Cancer Res. Treat., 106, 29-38 (2007), the disclosures of which are incorporated herein by reference. Preferably, the HER2 antigen is a portion of the extracellular domain of the HER2 protein. The HER2 antigen may be a heterologous antigen peptide sequence from the subject being treated. For example, a HER2 peptide sequence derived from a rat HER2 sequence can be employed in a composition for use in the treatment of a human subject. In other embodiments, the HER2 antigen is homologous to the species being treated in accordance with a method described herein. A number of human HER2 antigens found in the extracellular domain are listed below in Table I.

TABLE I

HER2 antigens found in the extracellular domain

| Epitope | Amino Acid Sequence |
|---|---|
| ECD 316-339 | PLHNQEVTAEDGTQRAEKCSKPCA (SEQ ID NO: 3) |
| ECD 485-503 | LFRNPHQALLHTANRPEDE (SEQ ID NO: 4) |
| ECD 605-622 | KPDLSYMPIWKFPDEEGA (SEQ ID NO: 5) |
| ECD 628-647 | INGTHSCVDLDDKGCPAEQR (SEQ ID NO: 6) |
| ECD P4 378-398 | PESFDGDPASNTAPLQPEQLQ (SEQ ID NO: 1) |
| ECD P6 544-560 | CRVLQGLPREYVNARHC (SEQ ID NO: 7) |
| ECD P7 610-623 | YMPIWKFPDEEGAC (SEQ ID NO: 8) |
| ECD 163-180 | YQDTILWKDIFHKNNQLA (SEQ ID NO: 9) |
| ECD 626 649 | KLLSLIKGVIVHRLEGVEGPSLCPINCTHSCV DLDDKGCPAEQRAS (SEQ ID NO: 10) |
| ECD 563-598 | CHPECQPQNGSVTCFGPEADQCVACAHYKDPP FCVA (SEQ ID NO: 11) |
| ECD 597-626 | VARCPSGVKPDLSYMPIWKFPDEEGACQPL (SEQ ID NO: 12) |

The epitopes in Table I are listed by their position in the extracellular domain (ECD) and in some cases by the sub-protein that they are found in. In some embodiments, the HER2 antigen comprises all or a portion of a P4 protein, a P6 protein, or a P7 protein, all of which form parts of the HER2 protein.

In some embodiments, the HER2 antigen can include a peptide sequence corresponding to an HER2 peptide including epitopes identified as recognition sites for both B-cells and helper T-cells. For example, antigenic HER2 peptides can include peptides having an amino acid sequence corresponding to a sequence located between position 163 and 182 of the HER2 protein. In some cases, various HER2 antigenic peptides can include overlapping sequences. In exemplary embodiments, HER2 antigens can include a peptide having the amino acid sequence YQDTILWKDIFHKNNQLALT (SEQ ID NO: 13) derived from human HER2 or YQDMVLWKDVFRKNNQLAPV (SEQ ID NO: 14) derived from rat HER2.

HER2 peptide antigens can be modified in ways that do not significantly interfere with their ability to generate an immune reaction. For example, HER2 peptide antigens can contain, for example, one or more D-amino acids in place of a corresponding L-amino acid; or can contain one or more amino acid analogs, for example, an amino acid that has been derivatized or otherwise modified at its reactive side chain. Similarly, one or more peptide bonds in the HER2 peptide antigen can be modified, or a reactive group at the amino terminus or the carboxy terminus or both can be modified. Such modified HER2 antigens can have improved ability to bind a linker group, as well as improved stability to a protease, an oxidizing agent or other reactive material the polypeptide may encounter in a living subject.

In certain embodiments, the anti-cancer particle can include a CPMV virus particle conjugated to a plurality of human HER2 peptide antigens having the amino acid sequence corresponding to $HER2_{163-182}$ (SEQ ID NO: 14). In an exemplary embodiment, chemical fusion can be used to produce CPMV-based HER2 anti-cancer particles, where a plurality of $HER2_{163-182}$ peptides (SEQ ID NO: 14) are conjugated to the exterior surface of CPMV virus particles.

The HER2 antigen(s) can be linked to the icosahedral-shaped plant virus particle by any suitable technique known to those skilled in the art for linking together a peptide and a protein. HER2 peptides can be coupled to an icosahedral plant virus particle or virus like particle either directly or indirectly (e.g. via a linker group). The location of the HER2 peptide antigen on the exterior can be governed by the amino acids of the viral coat protein, for example, CPMV capsid includes about 300 reactive lysine residues available for bioconjugation.

In some embodiments, the HER2 antigens are coupled to the plant virus particle using a linker group. HER2 antigens can be conjugated to the plant virus particle by any suitable technique, with appropriate consideration of the need for pharmacokinetic stability and reduced overall toxicity to the patient. A linker group can serve to increase the chemical reactivity of a substituent on either the agent or the virus particle, and thus increase the coupling efficiency, and can also improve the immunogenicity of the linked antigen. In some cases, the linker can include a short spacer consisting of 2 to 10 amino acids (e.g., glycine). For example, the linker group can include a short peptide linker, such as a LSPG peptide linker. Coupling can be affected, for example, through amino groups, carboxyl groups, sulfhydryl groups or oxidized carbohydrate residues. A preferred group suitable as a site for attaching antigens to the virus particle is lysine residues present in the viral coat protein.

The number of antigens linked to the plant virus particle will vary depending on the number of coat proteins in the icosahedral-shaped plant virus particle, and the availability of suitable reactive groups (e.g., amine, carboxyl, thiol) in the coat proteins. In some embodiments, the icosahedral-shaped plant virus particle is linked to from 2 to 1,000 HER2 antigens, while in other embodiments the virus particle is linked to from 5 to 100 HER2 antigens, or from 20 to 80, 20 to 70, 20 to 60, 20to 50, 20 to 40, or 25 to 35 HER2 antigens. In certain embodiments, a CPMV anti-cancer particle can include about 30 HER2 antigen peptides per CPMV.

In some embodiments, a suitable chemical linker group can be used. A linker group can serve to increase the chemical reactivity of a substituent on either the agent or the icosahedral-shaped virus particle or virus-like particle, and thus increase the coupling efficiency. Suitable linkage chemistries include maleimidyl linkers, which can be used to link to thiol groups, isothiocyanate and succinimidyl (e.g., N-hydroxysuccinimidyl (NHS)) linkers, which can link to free amine groups, diazonium which can be used to link to phenol, and amines, which can be used to link with free acids such as carboxylate groups using carbodiimide activation. Cysteine modified antigenic peptides using amine-to-sulfhydryl crosslinkers with aliphatic spacers that differ in chain lengths from 4.4 Angstrom to 9.4 Angstroms or crosslinkers with a PEG spacer varying in lengths form 17.6 Angstroms to 95.2 Angstroms, can also be used. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

In an exemplary embodiment, a HER2 peptide having amino acid sequence YQDTILWKDIFHKNNQLALT-LSPG-C (SEQ ID NO:16) or YQDMVLWKDVFRKNNQLAPV-LSPG-C (SEQ ID NO:17), which include a flexible LSPG linker and a terminal cysteine, are conjugated to CPMV using a two-step protocol using a bi-functional N-hydroxysuccinimide-PEG4-maleimide (SM-PEG4) linker (see FIG. 1A).

In other embodiments, the HER2 antigen is linked to the icosahedral-shaped plant virus particle through expression of a recombinant protein in plants using an N-terminal fusion on the coat protein. Methods for the preparation and isolation of recombinant fusion proteins are well known to those skilled in the art. For example, in one embodiment, the recombinant polypeptide includes a HER2 antigen having an amino acid sequence corresponding to amino acid residues about 162 to 183 of the human HER2 protein (i.e., SEQ ID NO:14). A recombinant polypeptide of the invention can be expressed from a recombinant polynucleotide or can be chemically synthesized. Preparation of recombinant HER2 antigens are described in U.S. Pat. No. 7,446,185.

In another aspect, the present invention provides a method of treating or decreasing the risk of developing an $HER2^+$ cancer in a subject by administering to a subject in need thereof an effective amount of an anti-cancer particle composition comprising an icosahedral plant virus or virus-like particle linked to a HER2 antigen. In some embodiments, the HER2+ cancer is characterized by the overexpression of HER2.

The present invention provides methods of stimulating an immune response in a subject against cells that express HER2 antigen. Cells that express HER2 can include tumor cancer cells or any other cells that express HER2, particularly cells involved in a pathologic condition. The disclosed methods are particularly useful for stimulating an immune response against cells that are involved in a pathologic condition and overexpress HER2 as compared to corresponding cells that are not involved in the pathologic condition. For example, the cells can be cancer cells that overexpress HER2 as compared to the level of HER2 expressed by normal cell counterparts to the cancer cells. In one embodiment, a method of stimulating an immune response in a subject against cancer cells that express HER2 is performed by administering an anti-cancer composition of the invention under conditions that result in the stimulation of an immune response by the anti-cancer composition against the HER2-expressing cells.

Stimulating an immune response in a subject using the anti-cancer particle compositions of the present invention can be used to either treat or decrease the risk of developing a HER2-expressing cancer, such as HER2 expressing cancer. In one embodiment, a method of stimulating an immune response in a subject against cancer cells that express HER2 is performed by administering an anti-cancer particle composition of the invention under conditions that result in the stimulation of both B-cell and a helper T-cell mediated immune response by the anti-cancer particle composition against the HER2 expressing cells.

When used to treat cancer, the anti-cancer particle composition is administered to a subject who has been diagnosed with cancer, in order to stimulate or increase an immune response against the cancer cells. The anti-cancer particle composition can be used as the sole method of treatment, or it can be combined with other methods of treating the cancer. Alternately, the anti-cancer particle composition can be administered to a subject who has not been diagnosed with cancer as a means of preventing or decreasing the risk or likelihood of cancer development. In some embodiments, the subject being treated and/or immunized using compositions described herein has been characterized as being a subject having a high or increased risk of developing cancer, such as an HER2-expressing cancer. Subjects can be characterized as being at high or increased risk of developing an HER2-expressing cancer as a result of, for example, family history, genetic testing, or high exposure to cancer-causing environmental conditions.

In some embodiments, the HER2 antigen is an antigen capable of generating a B-cell mediated immune response. A number of HER2 antigens have been identified that are capable of generating a B-cell-mediated immune response, in which antibodies are generated against the HER2 antigen. In this embodiment, vaccination provides active acquired immunity to a subject against HER2-expressing cancer. The immune system recognizes the plant virus particles linked to HER2 antigen as foreign, destroys them, and "remembers" the HER2 antigen through the generation of memory B cells. Memory B cells are a B cell sub-type that are formed within germinal centers following primary exposure to an antigen, and are important in generating an accelerated and more robust antibody-mediated immune response in the case of re-exposure to the antigen. Accordingly, when the immune system of a subject is exposed to HER2 antigen on cancer cells or cancer cell precursors, it is prepared to respond recognizing and destroying cells expressing or overexpressing the HER2 antigen before those cells can proliferate and form a tumor.

In some embodiments, the HER2 antigen is an antigen capable of generating a T-helper cell ($T_h$ cell, also known as a CD4+ cell) mediated immune response. HER2 antigens have been identified that include both B-cell and T-helper cell epitopes and can generate a T-helper cell mediated immune response in which phagocytes and cytotoxic CD8+ T-lymphocytes are activated, and various cytokines such as interferon gamma (IFNγ) and tumor necrosis factor (TNF) are released in response to antigen. CD4+ T cells are critical for initiating and maintaining the CTL response against tumors. CD4+ T helper cells activate APCs and enhance expression of MHC and co-stimulatory molecules such as IL-12 that are crucial for an effective CTL response. CD4+ T helper cells also secrete IL-2 that recruits CTLs to tumor sites. IFN-γ production by CD4+ T helper cells also upregulate the expression of MHC molecules on tumor cells leading to enhanced CTL recognition. In addition to supporting the primary CTL activity, CD4+ T helper cells also play a role in generating and maintaining memory CD8+ T cells, which are epigenetically programmed for more rapid and effective response upon re-stimulation with antigen.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In certain embodiments, cancers treated in accordance with a method described herein include HER2+ cancers including, but not limited to, carcinoma and sarcoma. In certain embodiments, the methods described herein include treatment of cancers such as breast, ovary, recto-colon, lung, prostate, stomach, pancreatic, and biliary cancers, all of which are HER2 expressing. The term "carcinoma" refers to a malignant new growth made up of epithelial cells tending to infiltrate surrounding tissues, and to give rise to metastases. A preferred type of cancer for treatment with the anti-cancer compositions of the present invention is HER2-expressing cancer, and in particular HER2-overexpressing cancer. HER2 expression refers to the expression of HER2 protein on the surface of the cell, where it can be recognized by the immune system. In an exemplary embodiment, the type of cancer for treatment with the anti-cancer compositions is HER2$^+$ breast cancer.

In some embodiments, the subject being administered a therapeutically effective amount of an anti-cancer plant virus particle is a subject who has been identified as having cancer. As is known to those skilled in the art, there are a variety of methods of identifying (i.e., diagnosing) a subject who has cancer. For example, diagnosis of cancer can include one or more of a physical exam, laboratory tests, imaging analysis, and biopsy. After cancer is diagnosed, a variety of tests may be carried out to look for specific features characteristic of different types and or the extent of cancer in the subject. These tests include, but are not limited to, bone scans, X-rays, immunophenotyping, flow cytometry, and fluorescence in situ hybridization testing. For example, typical methods of diagnosing HER2$^+$ breast cancer can include, but are not limited to, a physical exam, digital mammogram, breast MRI, breast ultrasound, stereotactic core and/or open tumor biopsy, as well as lab tests to determine if the tumor tissue expresses estrogen, progesterone, and/or HER-2/neu.

In some embodiments, the icosahedral-shaped plant virus or VLP is used to target cancer cells or cancer tissue in a subject. As used herein, targeting cancer tissue includes the ability of the anti-cancer virus particles to reach and preferably accumulate at the site of cancer, after being administered to the subject, for example, where the anti-cancer virus particles are systemically administered to a subject. The ability of icosahedral-shaped plant virus particles to target cancer tissue is supported by the in vitro cell uptake and animal model in vivo drug delivery studies carried out by the inventors. While not intending to be bound by theory, it appears that icosahedral-shaped plant virus particles are drawn to the leaky vasculature caused by the angiogenesis associated with rapid tumor growth, and this leaky vasculature encourages entry for anti-cancer plant virus particles through small pores, thereby delivering the anti-cancer plant virus particles to the cancer cells. As a result of this preferential accumulation, embodiments of the invention can deliver about 10%, about 20%, about 30%, about 40%, or even about 50% or more of the injected dose to tumor tissue.

In some embodiments, the administration of the plant virus particle can be proximal to a tumor and/or directly to the tumor site in the subject to provide a high local concentration of the icosahedral-shaped plant virus particle or plant virus-like particle linked to a HER2 antigen in the tumor microenvironment (TME) and/or in the tumor itself.

In some embodiments, a targeting moiety can also be attached to the icosahedral-shaped plant virus particle. By "targeting moiety" herein is meant a functional group which serves to target or direct the plant virus particle to a particular location, cell type, diseased tissue, or association. In general, the targeting moiety is directed against a target molecule. Thus, for example, antibodies, cell surface receptor ligands and hormones, lipids, sugars and dextrans, alcohols, bile acids, fatty acids, amino acids, peptides and nucleic acids may all be attached to localize or target the anti-lymphoma plant virus particle to a particular site. In some embodiments, the targeting moiety allows targeting of the plant virus particles of the invention to a particular tissue or the surface of a cell. Preferably, the targeting moiety is linked to the exterior surface of the icosahedral-shaped virus particle or VLP to provide easier access to the target molecule and does not significantly interfere with the function of the HER2 peptide antigens.

In some embodiments, the targeting moiety is a peptide. In further embodiments, the targeting moiety is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin.

In some embodiments, the antibody is directed against a cell-surface marker on a cancer cell; that is, the target molecule is a cell surface molecule. As is known in the art, there are a wide variety of cell surface molecules known to be differentially expressed on tumor cells. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242). In some embodiments, a cell surface molecule known to be differentially expressed on lymphoma cells is used. Examples of such cell surface markers include CD20, CD22, and CD40.

In some embodiments, a method of treating cancer described herein can include administering an additional therapeutic or cancer therapy to the subject. A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy.

In some embodiments, the method can include the step of administering a therapeutically effective amount of an additional anticancer therapeutic agent to the subject. Additional anticancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA. In some embodiments, cytotoxic compounds are included in an anticancer agent described herein. Cytotoxic compounds include small-molecule drugs such as doxorubicin, methotrexate, vincristine, and pyrimidine and purine analogs, referred to herein as antitumor agents. In particular embodiments, an additional anticancer therapeutic agent can include a corticosteroid such as but not limited to prednisone.

The additional anticancer therapeutic agent can include an anticancer or an antiproliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anticancer therapeutic agents that can be administered in combination with an anti-cancer icosahedral plant virus or virus-like particle described herein include Taxol, Adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon α-2a; interferon α-2b; interferon α-n1; interferon α-n3; interferon β-I a; interferon γ-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In certain embodiments, additional therapeutic agents administered to a subject for the treatment of HER2 cancer as described herein can include one or more of emtansine, an anthracycline, such as adriamycin, an alkylating agent such as Cytoxan (cyclophosphamide), an antimetabolite such as Fluorouracil (5FU), and a taxane, such as Taxol or Taxotere.

In some embodiments, the anti-cancer therapy administered to the subject in addition to the anti-cancer plant virus particles can include the cancer ablation therapy. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins. Another method of ablating cancer such as breast cancer that has been treated with an anti-cancer particle composition of the present invention is to conduct surgery to remove the cancer tissue (e.g., breast cancer tissue) from the subject. Types of surgery for breast cancer vary depending on the nature of the breast cancer, and include lumpectomy, partial or segmental mastectomy or quadrantectomy, simple or total mastectomy, radical mastectomy, and modified radical mastectomy. Appropriate surgeries for treating other types of HER2$^+$ cancer are known to those skilled in the art.

In some embodiments, ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers). In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanized or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations. In some embodiments, a monoclonal antibody is administered in combination with a chemotherapeutic agent such as emtansine (e.g.,ado-trastuzumab emtansine).

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies that can be used together with the virus or virus-like particles of the invention for cancer treatment.

Immunotherapy administered in combination with the anti-cancer particles described herein can include therapies that attract immune cells into the tumor TME and thus improve the efficacy of the icosahedral-shaped plant virus-HER2 antigen anti-cancer particles. It was shown that a combination of CPMV administered subcutaneously and CPMV-HER2 antigen anti-cancer particles administered intratumorally significantly slows tumor growth and provides a greater survival benefit than either single agent (see FIG. 5C). It is believed the in situ administration enhances the potency of the tumor antigen specific antibodies by enriching the effector cells in the TME.

Therefore, in another aspect, the present invention provides a method of treating or decreasing the risk of developing an HER2+ cancer or a cancer characterized by the overexpression of HER2 in a subject, by administering to a subject in need thereof an effective amount of an anti-cancer particle composition comprising an icosahedral plant virus or virus-like particle (VLP) linked to a HER2 antigen and administering in situ to the cancer of the subject a therapeutically effective amount of an icosahedral-shaped plant virus or plant virus-like particle, such as CPMV. In situ administration of immunostimulatory plant virus or plant virus like particles, i.e., particles that are not linked to a HER2 antigen, includes directly administering the plant virus particles into, or proximal to, an identified tumor to modulate the local TME from an immune-suppressive to an immune-supportive environment, resulting in infiltration and activation of immune effector cells leading to a local and systemic anti-tumor response.

In some embodiments, ablating the cancer includes administering a therapeutically effective amount of radiotherapy (RT) to the subject. In some embodiments, RT is administered prior to administration of the icosahedral-shaped plant virus nanoparticle. In some embodiments, administering to the cancer, (e.g., at a tumor site) a therapeutically effective amount of a icosahedral-shaped plant virus or virus-like particle linked to HER2 antigen to the subject in combination with administering radiotherapy to the subject can result in an increase in tumor infiltrating lymphocytes (TILs), such as tumor infiltrating neutrophils (TINs) at the tumor site of the subject.

Radiotherapy uses high-energy rays to treat disease, usually x-rays and similar rays (such as electrons). Radiotherapy administered to a subject can include both external and internal. External radiotherapy (or external beam radiation) aims high-energy x-rays at the tumor site including in some cases the peri-tumor margin. External radiotherapy typically includes the use of a linear accelerator (e.g., a Varian 2100C linear accelerator). External radiation therapy can include three-dimensional conformal radiation therapy (3D-CRT), image guided radiation therapy (IGRT), intensity modulated radiation therapy (IMRT), helical-tomotherapy, photon beam radiation therapy, proton beam radiation therapy, stereotactic radiosurgery and/or sterotactic body radiation therapy (SBRT).

Internal radiotherapy (brachytherapy) involves having radioactive material placed inside the body and allows a higher dose of radiation in a smaller area than might be possible with external radiation treatment. It uses a radiation source that is usually sealed in an implant. Exemplary implants include pellets, seeds, ribbons, wires, needles, capsules, balloons, or tubes. Implants are placed in your body, very close to or inside the tumor. Internal radiotherapy can include intracavitary or interstitial radiation. During intracavitary radiation, the radioactive source is placed in a body cavity (space), such as the uterus. With interstitial radiation, the implants are placed in or near the tumor, but not in a body cavity.

In some embodiments, an immune checkpoint inhibitor can be further administered to eradicate suppressive regulatory T cells, for example prior to RT, although RT is not required. Exemplary checkpoint inhibitors can include CTLA4 and PD-1/PDL-1 inhibitors. The cytotoxic T-lymphocyte-associated antigen 4 (CTLA-4) and programmed death 1 (PD-1) immune checkpoints are negative regulators of T-cell immune function and inhibition of these targets, results in increased activation of the immune system. Therefore, in some embodiments, a checkpoint inhibitor administered to a subject can include a CTLA-4 and/or PD-1 inhibitor. For example, Ipilimumab, an inhibitor of CTLA-4, is approved for the treatment of advanced or unresectable melanoma. Nivolumab and pembrolizumab, both PD-1 inhibitors, are approved to treat patients with advanced or metastatic melanoma and patients with metastatic, refractory non-small cell lung cancer. In addition, the combination of ipilimumab and nivolumab has been approved in patients with BRAF WT metastatic or unresectable melanoma. In some embodiments, an immune checkpoint agonistic agent, such as an OX40 agonistic agent, can be further administered can be administered promote immune activation of cytotoxic T-cells.

It has been shown that moderate magnetic nanoparticle hyperthermia (mNPH) treatment administered to a tumor can generate immune-based systemic resistance to tumor rechallenge. Therefore, in some embodiments, a therapeutically effective amount of a moderate magnetic nanoparticle hyperthermia (mNPH) treatment can be administered to the subject in combination with an anti-cancer plant virus particle or virus-like particle and/or radiotherapy, wherein the mNPH is activated with an alternating magnetic field (AMF) to produce moderate heat. Without being bound by theory, it is believed that plant virus-like particle immune adjuvants, such as a plant virus nanoparticles described herein and/or a mNPH, will combine with RT-induced generation of immunogenic cell death (ICD) to expand the tumor specific effector T cell population causing longer local and distant tumor remission.

A mNPH treatment can include the use of a magnetic iron oxide nanoparticle (IONP). Once administered to the subject intratumorally, the mNPH can, in some embodiments, be activated with an alternating magnetic field (AMF) to produce moderate heat (e.g., 43°/60° min) at the tumor site. In some embodiments, the RT is hypofractionated RT (HFRT) that delivers larger but fewer doses/fractions than typical RT therapies.

In order to evaluate the efficacy of the HER2 antigen-presenting anti-cancer icosahedral-shaped plant virus particles described herein, challenge studies can be conducted. Such studies involve the inoculation of groups of test animals (such as mice) with a HER2 antigen-presenting anti-cancer plant virus particle by standard techniques. Control groups comprising non-inoculated animals and/or animals inoculated with a commercially available vaccine, or other positive control, are set up in parallel. After an appropriate period of time post-vaccination, the animals are challenged with a cancer cells. Blood samples collected from the animals pre- and post-inoculation, as well as post-challenge are then analyzed for an antibody response and/or T cell response to the HER2 antigen. Suitable tests for the T and B cell responses include, but are not limited to, Western blot analysis and Enzyme-Linked Immunosorbent Assay (ELISA) assay. Cellular immune response can also be assessed by techniques known in the art, including monitoring T cell expansion and IFN-γ secretion release, for example, by ELISPOT to monitor induction of cytokines.

The animals can also be monitored for development of other conditions associated with cancer including, for example, growing tumor size, and the like, for certain HER2 cancer cell lines, survival is also a suitable marker.

When used in vivo, the anti-cancer plant virus particles and/or additional anti-cancer therapeutic agents described herein can be administered as a pharmaceutical composition, comprising a mixture, and a pharmaceutically acceptable carrier. The anti-cancer virus particles may be present in a pharmaceutical composition in an amount from 0.001 to 99.9 wt %, more preferably from about 0.01 to 99 wt %, and even more preferably from 0.1 to 95 wt %.

The anti-cancer plant virus particles, or pharmaceutical compositions comprising these particles, may be administered by any method designed to provide the desired effect. Administration may occur enterally or parenterally; for example orally, topically, rectally, intracisternally, intravaginally, intraperitoneally or locally. Parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, intraperitoneal injection, intracranial and intrathecal administration for CNS tumors, and direct application to the target area, for example by a catheter or other placement device. In some embodiment, the anti-cancer particles may be administered topically. Anti-cancer particles can be topically administered passively for example, by direct application of an ointment or a skin patch, or administered actively, for example, using a nasal spray or inhalant, in which case one component of the composition is an appropriate propellant or through the use of facilitated absorption through the skin using, for example, transdermal iontophoresis. In a particular embodiment, the anti-cancer particles are administered are administered to the subject by subcutaneous injection.

When formulated as separate compositions, "combination therapy" described herein are intended to embrace administration of these therapeutic agents in a sequential manner, that is, wherein each therapeutic agent is administered at a different time, as well as administration of these therapeutic agents, in a substantially simultaneous manner. For example, administration of an anti-cancer particle is carried out in a substantially simultaneous manner as CPMV particle immunostimulatory agent administration. Sequential or substantially simultaneous administration of each therapeutic agent can be effected by any appropriate route including, but not limited to, intratumoral routes, intraperitoneal routes, subcutaneous routes, oral routes, intravenous routes, intramuscular routes, and direct absorption through mucous membrane tissues. A preferred method for administering the plant virus or virus-like particle and one or more immune checkpoint modulating agents to a subject having cancer is by intratumoral injection. However, the therapeutic agents can be administered by the same route or by different routes. For example, anti-cancer particles of the combination selected may be administered by subcutaneous injection while the immunostimulatory agent(s) of the combination may be administered intratumorally. Alternatively, for example, all therapeutic agents may be administered by intratumorally injection. The sequence in which the therapeutic agents are administered is not narrowly critical.

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The pharmaceutical compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

Suitable pharmaceutically acceptable carriers may contain inert ingredients that do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

A pharmaceutically acceptable carrier for a pharmaceutical composition can also include delivery systems known to the art for entraining or encapsulating drugs, such as anti-cancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

Suitable doses can vary widely depending on the therapeutic being used. A typical pharmaceutical composition for intravenous administration would be about 0.1 mg to about 10 g per subject per day. However, in other embodiments, doses from about 1 mg to about 1 g, or from about 10 mg to about 1 g can be used. Single or multiple administrations of the compositions may be administered depending on the dosage and frequency as required and tolerated by the subject. In any event, the administration regime should provide a sufficient quantity of the composition of this invention to treat the subject effectively.

Useful dosages of the additional anticancer agents, such as antimitotic agents, immunostimulatory agents, and anti-cancer plant virus particles can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the additional anti-cancer agents and/or anti-cancer plant virus particles vary depending upon many different factors, including means of administration, target site, physiological state of the patient, whether the patient is human or an animal, other medications administered, and whether treatment is prophylactic or therapeutic.

The formulations may be conveniently presented in unit dosage form and may be prepared by any of the methods well known in the art of pharmacy. Preferably, such methods include the step of bringing the anti-cancer plant virus particles into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect.

One skilled in the art can readily determine an effective amount of anti-cancer plant virus particles and/or additional cancer therapeutics to be administered to a given subject, by taking into account factors such as the size and weight of the subject; the extent of disease penetration; the age, health and sex of the subject; the route of administration; and whether the administration is local or systemic. Those skilled in the art may derive appropriate dosages and schedules of administration to suit the specific circumstances and needs of the subject. For example, suitable doses of the anti-cancer virus particles to be administered can be estimated from the volume of cancer cells to be killed or volume of tumor to which the virus particles are being administered.

Useful dosages of the active agents can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the plant virus particles vary depending upon many different factors, including means of administration, target site, physiological state of the patient, whether the patient is human or an animal, characteristics of the subject, such as general health, age, sex, body weight and tolerance to drugs as well as the degree, severity and type of cancer, other medications administered, and whether treatment is prophylactic or therapeutic. The skilled artisan will be able to determine appropriate dosages depending on these and other factors using standard clinical techniques.

For example, in some embodiments, the therapeutically effective amount of icosahedral-shaped anti-cancer particles described herein is the amount effective to overcome self-tolerance against the HER2 antigen on HER2+ cancer cells in the subject. In some embodiments, the therapeutically effective amount of icosahedral-shaped anti-cancer particles described herein is the amount effective to promote a potent B-cell and CD4+ T-helper cell response in the subject. In some embodiments, the therapeutically effective amount of icosahedral-shaped anti-cancer particles described herein is the amount effective to delay tumor growth in the subject and/or prolong survival of the subject.

The methods described herein contemplate single as well as multiple administrations, given either simultaneously or over an extended period of time. A pharmaceutically acceptable composition containing the anti-cancer virus particles and/or additional cancer therapeutic can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, the pharmaceutically acceptable composition containing the anti-cancer plant virus particles and/or an additional cancer therapeutic is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased.

For example, the administration of anti-cancer virus particles and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

In an exemplary embodiment, anti-cancer HER2 plant virus particles are administered to the subject in need thereof via subcutaneous injection once a week for about two to about four weeks to properly immunize the subject.

In some embodiments, the frequency of administration of anti-cancer plant virus particles can pose challenging for clinical implementation. Therefore, in some embodiments, the anti-cancer virus particles administered to a subject can be formulated in a slow release formulation in order to sustain immune stimulation by maintaining a therapeutic concentration of the anti-cancer virus particles, (e.g., at the site of a tumor) while alleviating the need for frequent administrations. In some embodiments, a slow release formulation can include a polymer-based hydrogel or a dendrimer.

In some embodiments, a slow-release formulation can include an anti-cancer plant virus or plant virus like particle dendrimer hybrid aggregate. The dendrimer can include a positively-charged polyamidoamine (PAMAM) dendrimer, such as a medium-sized generation 3 (G3) or generation 4 (G4) PAMAM dendrimer. Depending on the specific application, the plant virus-like particle-dendrimer hybrid aggregates can vary in size and release rate of the plant virus-like particle from the dendrimer when administered to a subject. In some embodiments, the anti-cancer plant virus particle-dendrimer hybrid aggregates are formulated so that at low salt the assembly of the aggregates is triggered and while under physiologic salt concentrations disassembly and anticancer plant virus particle release is induced.

Examples have been included to more clearly describe particular embodiments of the invention. However, there are a wide variety of other embodiments within the scope of the present invention, which should not be limited to the particular examples provided herein.

EXAMPLE

We evaluated the potency of Cowpea mosaic virus (CPMV) nanoparticle-based cancer vaccine in several mouse models of HER2+ tumors in conjugation with the antigenic CH401 peptide derived from the extracellular domain of HER2 receptor. We evaluated the vaccine efficacy in the settings of ectopic and orthotopic primary tumor challenge as well as with a metastatic tumor challenge using the aggressive DDHER2 cells in Balb/c mice. We also evaluated the efficacy of the vaccine against a transplantable tumor derived from transgenic MMTV-neu mice that develop spontaneous HER2+ tumors. Furthermore, we evaluated the potential for synergy of the CPMV-HER2 vaccine when combined with an in situ vaccine strategy involving CPMV particles. Efficacy studies were paralleled with immunological studies to gain insights into the mechanism of the cancer vaccine.

Methods

VNP Propagation: Established procedures were used for the propagation and purification of CPMV. Purified VNPs were stored in potassium phosphate buffer (0.1 m, pH 7.0) at 4° C. Concentrations of VNPs were determined by UV spectroscopy at 260 nm using the molar extinction coefficients $^\varepsilon$CPMV=8.1 mL mg$^{-1}$ cm$^{-1}$.

Synthesis of the CPMV Vaccine Formulation

Human HER2 epitope CH401and the rat analogue with GPSL linker and terminal Cysteine residue were procured from Genscript: Human$_{163-182}$: YQDTILWKDIFHKNNQLALT-GPSL-C (SEQ ID NO: 15) versus Rat$_{167-186}$: YQDMVLWKDVFRKNNQLAPVGPSL-C (SEQ ID NO: 16). In a two-step protocol, cysteine-terminated peptide epitopes with flexible GPSL linker were conjugated to VNPs via the heterobifunctional N-hydroxysuccinimide-PEG4-maleimide linker SM-PEG4 (Life Technologies). Briefly, CPMV was reacted with 3500 molar excess of SM-PEG4 linker at room temperature for 2 h at a 2 mg mL$^{-1}$ CPMV concentration followed by a 5000 molar excess of peptides overnight. CPMV-CH401 formulations were purified over a 40% w/v sucrose cushion at 160 000×g for 3 h and resuspended in sterile PBS.

Vaccine Characterization

To verify peptide conjugation, unmodified CPMV, CPMV-SM(PEG)4 intermediate, and purified CPMV-CH401 (20 μg of each) were compared by SDS electrophoresis using pre-cast NuPAGE 4-12% Bis-Tris proteins gels (ThermoFisher Scientific). AlphaImage gel documentation system (Protein simple) was used to capture image of gel stained with GelCode Blue Safe protein stain (ThermoFisher Scientific) and lane density analysis (ImageJ 1.44o software) was used to quantify peptide conjugation. Particle integrity was confirmed by transmission electron microscopy (TEM) using FEI Tecnai F30 instrument following uranyl acetate staining.

Immunizations

All animal experiments were carried out in accordance with Case Western Reserve University's Institutional Animal Care and Use Committee. 7-8 week old female Balb/cmice (Charles River, N.J.) or FVB/N mice (Jackson lab) were immunized with 50 μg CPMV-CH401 vaccine or CH401 peptide (2 μg) in PBS (100 μL) through subcutaneous injections. Blood was collected through retro-orbital bleeding and centrifuged at 14,800 rpm for 10 min to separate the serum, which was then stored at 4° C. until analyzed.

Antibody Titers and Isotypes

ELISAs were carried out to determine levels of CH401 peptide specific IgG titers and HER2 specific IgG isotypes. Peptide-specific IgG ELISA was performed on the 96-well Pierce Maleimide Activated Plates (Thermo Fisher Scientific) prepared and processed as per manufacturer's instructions and coated with CH401 peptide (1 μg per well). Sera from immunized mice at various dilutions were incubated in the wells at 37° C. for 2 h. Plates were washed four times with washing buffer (0.05% v/v Tween-20 in PBS, 200 μL per well) between all steps. Plates were then incubated with 100 μL of alkaline phosphatase-labeled goat anti-mouse IgG (Invitrogen, Thermo Fisher Scientific) in blocking buffer (at 1:3000 dilution) at 37° C. for 1 h and developed with 100 μL of 1-step PNPP substrate (Thermo Fisher Scientific) for 10 min at 4° C. Reaction was stopped using 2 m NaOH (50 μL). Absorbance was then read at 405 nm using a Tecan microplate reader. IgG isotyping was similarly performed against HER2 protein using Ni-activated plates coated according to manufacturers' instructions with 1μg recombinant rat or human HER2/ ErbB2 protein containing His-tag (Acro Biosystems, Newark, Del.).

Cell Lines

DDHER2 cell line was a gift from Dr. Darrel Irvine's lab at MIT, Cambridge-Mass. Cells were maintained on DMEM media containing 25 mm HEPES and supplemented with 10% v/v fetal bovine serum and 1% v/v Penicillin/Streptomycin (all reagents from Life Technologies, Grand Island, N.Y.) at 37° C. and 5% CO$_2$. DDHER2-Luc cell line used for in vivo tracking was generated by stably transfecting DDHER2 cells using transformation protocol described previously.

Cell Binding Assay

For confocal studies, 25, 000 DDHER2 cells per well were cultured on glass coverslips in a 24-well suspension culture plate for 24 h. Pooled antisera from immunized mice were added with fresh culture media (1:100 dilution) and incubated with cells at 4° C. for 2 h. Post-incubation, cells were washed, fixed, and stained with goat anti-mouse-AlexaFluor 488 secondary antibody (1:1000 dilution; Life Technologies). Confocal images were captured on an Olympus FluoView™ FV1000 LSCM and data processed using ImageJ 1.44o software. Cell binding was quantified using flow cytometry. DDHER2 cells were collected in enzyme-free Hank's-based Cell Dissociation Buffer (Fisher), and resuspended in 200 μL of complete medium in a 96-well plate at 200 000 cells per well, then incubated for 2 h at 4° C. with sera from naive and immunized mice (1:100 dilutions). Post-incubation, cells were washed twice in FACS buffer (1 mm EDTA, 25 mm HEPES, 1% v/v FBS in PBS, pH 7.0), fixed in 2% v/v paraformaldehyde and washed twice again, then stained with goat anti-mouse IgG antibody conjugated with AlexaFluor 488 (1: 1000 dilution) for 60 min at 4° C. BD LSR II Flow Cytometer was used for cytometry and FlowJo v8.6.3 software used for analyses.

Complement-Dependent Cytotoxicity

DDHER2 cells re-suspended in 200 μL FACS buffer in a 1.5-mL Eppendorf tube (at 80,000 cells per tube) were incubated for 1 h at 4° C. with mouse serum diluted 1:50 with FACS buffer or similar dilutions of rabbit polyclonal anti-HER2 Ab (Novus Biologicals). After three times washing with PBS, the cells were re-suspended in 200 μL serum-free medium and transferred to 96-well plates in four replicates (20 000 cells per well in 50 μL medium). Rabbit C12CC complement (BioRad) was diluted 1:20 in serum-free medium and added to the plate (50 μL per well). Rabbit complement inactivated by heating at 65° C. for 30 min was incubated with cells that had not been exposed to mouse serum as a control representing 100% cell viability. Cells were incubated at 37° C. with 5% $CO_2$ for 4 h before adding 100 μL per well of 0.5% methylthiazolyldiphenyl-tetrazolium bromide (MTT) in PBS. After incubation at 37° C. for 2 h, the solution was carefully removed and 100 μL per well of DMSO was added before measuring the absorbance at 490 nm on a Tecan microplate reader.

Vaccine Efficacy Studies

Female Balb/c mice were challenged with $2 \times 10^6$ DDHER2 cells in 50 μL sterile PBS under anesthesia using a Hamilton needle in the mammary fat pad. Sutures were applied to close the wound and mice were administered with Carpofen (5 mg $kg^{-1}$) subcutaneously for 3 days post surgery and observed for any discomfort for 72 h. Mice were monitored for appearance of palpable tumors and later tumors were measured using digital calipers. Tumor volumes were calculated as 0.5*(length×width2); a 1000 mm3 volume was considered end point volume and mice were euthanized thereafter. For subcutaneous tumors, $2 \times 10^6$ DDHER2 cells (in 100 μL of DMEM+Matrigel) were inoculated under the skin on right flank using a 26-gauge needle. Tumors were monitored as above. For metastatic studies, $1 \times 10^6$ DDHER2 cells in 200 μL of sterile PBS with 0.3% FBS were injected intravenously through tail vein. Tumors were monitored using bioluminescence imaging. Mice were injected intraperitoneally with luciferin (15 mg $mL^{-1}$, 150 μL) and imaged 5 min post-injection using a PerkinElmer IVIS Spectrum in vivo imaging system. For FVB/N studies, tumors derived from transgenic FVB/N (MMTVneu) mice were cut into 2.5-3 mm pieces and were surgically implanted into mammary fat pad. Following surgery, similar precautions were taken as above and tumors were monitored similarly. For in situ vaccination, subcutaneous tumors were injected with 100 μg of CPMV in 20 μL of sterile PBS using a 30 gauge, 0.5 inch needle. The needle was retracted slowly to avoid any solution loss. Detailed dosing information and administration scheduled are provided in the main text of the manuscript.

Splenocyte Isolation, Ex Vivo Stimulation, and Flow Cytometry

Immunized and nonimmunized mice (n=5) were euthanized 7 days after last vaccination and spleens were harvested under aseptic conditions in ice cold RPMI media. Single cell suspension was obtained by passing the spleens through 40 μm cell restrainer. Cells were then rinsed and spun at 200 g for 5 min, supernatant was discarded and pellet resuspended in 5 mL of RBC lysis buffer on ice for 5 min. Reaction was stopped by diluting the lysis buffer. Cells were centrifuged and re-suspended in RPMI media and counted. Splenocytes ($10^6$ cells per mL) were re-stimulated with 20 μg of CH401 peptide for 24 h at 37° C. For the last 5 h brefeldin A (10 mg $mL^{-1}$) was added into the medium. Cells were then washed in PBS and resuspended in staining buffer (PBS 2% FBS, 0.1% sodium azide). Surface staining was performed for 30 min at 4° C. in dark with the following fluorescently labeled antibodies: Pacific blue-CD45 (30-F11), APC/Cy7-$CD3_\varepsilon$ (145-2V11 A); FITC-CD4 (GK1.5), APC-CD8α (53-6.7), PECD44 (IM7), and isotype controls (Biolegend). Then, cells were fixed in 3% paraformaldehyde, permeabilized with 0.1% saponin, then incubated with PE/Cy7-anti-IFN-γ (XMG1.2) Ab (BioLegend) for 30 min in 0.1% saponin. Cells were washed twice and resuspended in staining buffer before acquisition. Flow cytometry analyses were performed on a BD LSRII cytometer (BD Biosciences), and data were analyzed using the FlowJo software. OneComp eBeads (eBiosciences) were used as compensation controls.

Statistical Analysis

All statistical analyses were performed using the GraphPad Prism 7 software. For immunogenicity studies (FIG. 1), following groups were compared: CPMV-CH401H (n=9), CPMV-CH401R (n=10), CH401H (n=10), CH401R (n=10). All ELISAs were performed using pooled sera from treatment groups in three replicates/ sample. Data are plotted as mean with SEM. Statistical significance between the groups were compared by 2way ANOVA using Tukey's multiple comparisons test and p-values have been reported (**$p<0.0001$, *$p<0.001$, **$p<0.01$, *$p<0.05$ and ns=no significance). Flow cytometry experiments were performed on cells in three replicates/ sample, data analyzed using ordinary one-way ANOVA (**$p<0.0001$). Cytotoxicity analyses was performed in four replicates/ sample, data analyzed with ordinary oneway ANOVA ($p<0.0001$; *$p<0.001$). For in vivo vaccine efficacy using orthotropic model in Balb/c mice (FIG. 2A-C), mice were immunized with CPMV-CH401R (n=10) and CPMV-CH401H vaccines (n=9) or free peptides (n=10) or PBS (n=10). Data is plotted as mean with SEM to day where n≥5 for each group. Statistical analysis between tumor volumes on days 20, 30, 40, and 55 was performed using ordinary one-way ANOVA using Tukey's multiple comparison (**$p<0.01$, *$p<0.05$). For subcutaneous tumor studies (FIGS. 2D-F), n=10 was used for all three groups. Data is plotted to day where n≥5 for each group. Statistical analysis between tumor volumes on days 30 was performed using ordinary one-way ANOVA using Tukey's multiple comparison (**$p<0.0001$, $p<0.01$). Overall survival benefits between the immunized and control group was compared using Kaplan-Meier plot. Statistical analysis on the survival curves was performed using Log-rank (Mantel-Cox) test (***$p<0.001$, *$p<0.05$). For lung metastases study PBS (n=3), CPMV-CH401 vaccine (n=5) and CH401 (n=5) were compared. Bioluminescence signal intensities were compared using ROI analysis (total counts) performed with the Living Image Software (PerkinElmer). Statistical analysis between treatment groups was performed using two-way ANOVA using Tukey' smultiple comparison test (***$p<0.001$, *$p<0.05$). For transplant tumor studies (FIG. 3), n=10 female FVB mice were used for all groups. Tumor growth monitoring data is plotted as scatter dot plot with mean and SD. Kaplan-Meier plot have been used to compare the survival benefits offered by the vaccine over control mice. Statistical analysis on the survival curves was performed using Log-rank (Mantel-Cox) test ($p<0.01$). For splenocyte analyses using flow cytometry (FIG. 4) n=5 mice per group used. Ex vivo stimulation and staining for flow cytometry was performed in triplicates. Cytometry data were analyzed using the FlowJo software. Data is plotted as averages and SD; statistical analysis was performed by oneway ANOVA using Tukey's multiple comparison test with, $p<0.005$, *$p<0.05$. For combination therapy (FIG. 5) n=10 was used for all groups except PBS s.c/ PBS i.t. (n=8). Tumor volumes were plotted to days where n≥5. Statistical analysis was performed by ordinary one-way ANOVA using Tukey's multiple comparison tests (**$p<0.0001$, $p<0.001$, *$p<0.01$). C) Kaplan-Meier plot compared the survival benefits; statistical analysis on the survival curves was performed using Log-rank (Mantel-Cox) test (**p<0.0001; *p<0.001, *p<0.05).

RESULTS

In this example, we established the chemistry for formulating a plant virus-based HER2 vaccine candidate using the 30 nm-sized icosahedral nanoparticles from CPMV. Specifically, CPMV was engineered to display the HER2 epitope CH401, a potent epitope from the extracellular domain of HER2 containing an anchoring motif of MHC class II molecule. The CH401 peptide contains epitopes for both B-cells and helper T-cells. In our previous work, we demonstrated that immunization of female FVB/N mice with this CPMV-CH401 vaccine led to high titers of HER2-reactive antibodies spanning the IgG1/2a/2b isotypes.

With the chemistry of the CPMV-HER2 vaccine well established, in this work, we evaluated the anti-tumor activity of CPMV-CH401 vaccine in several mouse models of HER2+ tumors to validate the potency of this vaccine candidate.

Synthesis and Immunogenicity of CPMV-CH401 Vaccine

All animal experiments were carried out in accordance with Case Western Reserve University's Institutional Animal Care and Use Committee. CPMV was propagated in and purified from black-eyed peas using established methods we reported previously. The CPMV capsid is a 30 nm-sized icosahedron containing 60 copies each of a large (L, 42 kDa) and small (S, 24 kDa) coat protein arranged with pT=3 icosahedral symmetry. The CH401 peptide, designed with a flexible GPSL linker and a C-terminal cysteine, was conjugated to CPMV via its solvent exposed Lys side chains using a bi-functional N-hydroxysuccinimide-PEG4-maleimide (SM-PEG4) linker. The conjugation was as previously reported (FIG. 1A). The resulting CPMV-CH401 particles remained structurally sound as determined by transmission electron microscopy (FIG. 1B). Denaturing gel electrophoresis confirmed conjugation of CH401 to the CPMV coat protein (CP) as indicated by the appearance of additional higher molecular weight bands above the small CP (FIG. 1C). The protein band intensity analysis indicated modification of nearly 50% of S-CP, which corresponds to ≈30 CH401 peptides per CPMV (FIG. 1C). The modification of large coat protein is not clear enough for quantitative analysis.

The human HER2 protein erbB2 and the rat counterpart neu share 88% homology (UniProt P04626 and P06494, respectively). The 20-mer rat neu sequence homologue to the human CH401163-182 domain differ in five amino acids (human$_{163-182}$: YQDTILWKDIFHKNNQLALT) (SEQ ID NO:13) versus rat$_{167-186}$: YQDMVLWKDVFRKNNQLAPV)(SEQ ID NO:14). Earlier studies have compared cross-reactivity of human HER2 and rat neu in vaccine formulations. These results have indicated that in transplantable tumor models homologous vaccines are more efficient over heterologous vaccines. On the contrary, in transgenic mouse models of HER2 tumors and in clinical studies, it has been demonstrated homologous vaccines are unable to break self-tolerance of HER2. In this work we compared efficacy of CPMV-CH401 formulations with human (H) versus rat (R) versions of the CH401 epitope. Female Balb/c mice (n=10) were immunized subcutaneously with a 50 μg per injection dose of CPMV-CH401H or CPMV-CH401R vaccines in PBS; the administration schedule (FIG. 1D) was four biweekly treatments.

Figure 1E:
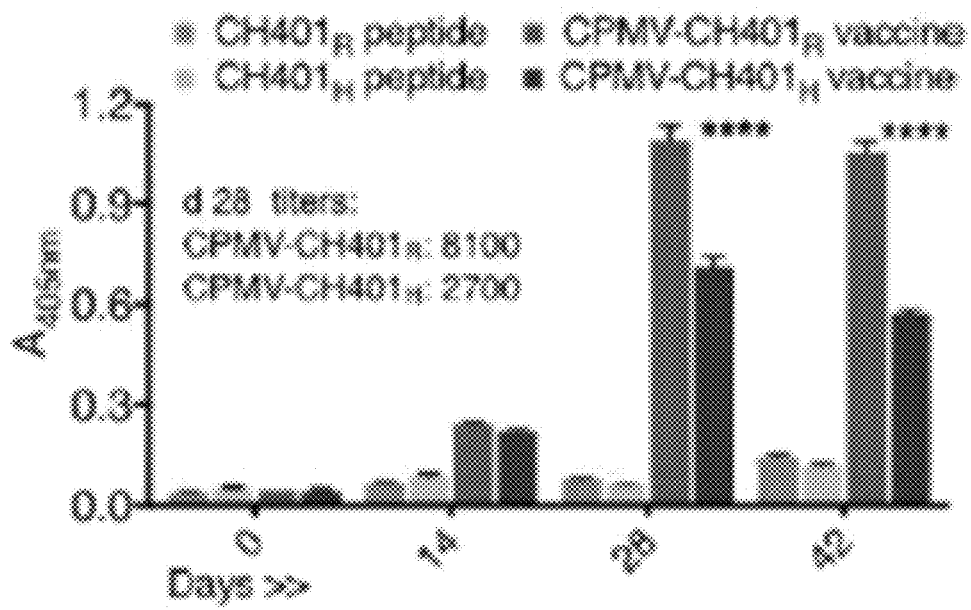
Figure 1F:
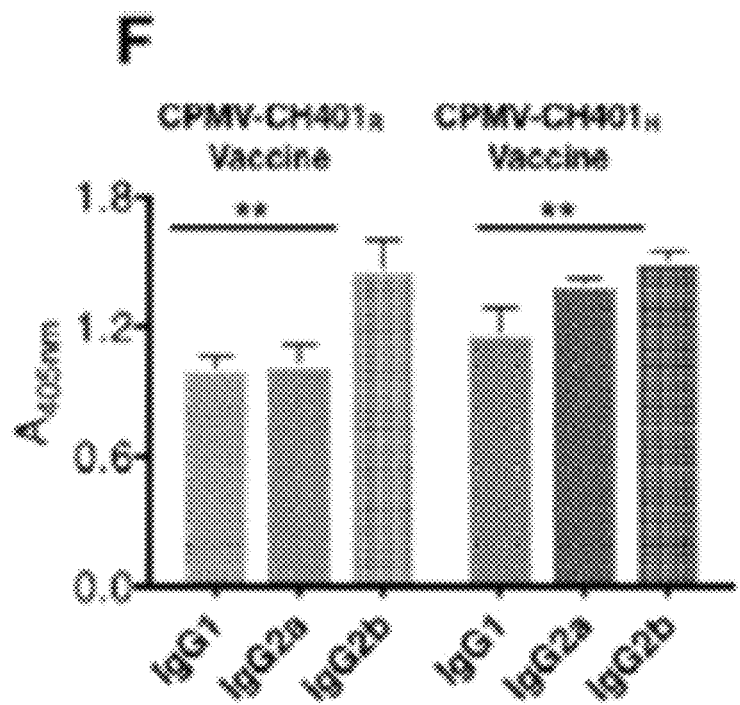

Corresponding quantities of free peptides in PBS were also administered. Sera were collected from all mice prior to first immunization and then on each day of vaccination for analysis (FIG. 1D). ELISAs performed on CH401-coated plates showed a steady increase in the CH401-specific IgG titers with successive immunizations; the titers peaked on day 28, indicating that a single booster dose is sufficient to generate a maximal titer (FIG. 1E). As expected, CH401-specifc IgG titers from free peptide immunizations remained comparable to pre-immunization sera highlighting the need for an immunostimulatory carrier for delivery of the short peptides (FIG. 1E). Between the formulations, immunization with CPMV-CH401R resulted in significantly stronger rat and human CH401-specific IgG response compared to CPMV-CH401H (FIG. 1E) with threefold higher peak titers (8100 versus 27,000 for CPMV-CH401R versus CPMV-CH401H tested against rat CH401; FIG. 1E) suggesting stronger immunogenicity of the rat peptide in the mouse model. Next, IgG isotyping performed on recombinant rat HER2 protein coated plates revealed the presence of IgG1, IgG2a, and IgG2b isotypes in mouse sera from both the rat and human CH401 vaccine formulations (FIG. 1F). Both vaccine formulations stimulated comparable levels of IgG1 and IgG2a isotypes and significantly higher levels of IgG2b (FIG. 1F). Thus, the CPMV-based vaccines produced a broad spectrum of IgG isotypes including high IgG2a/2b titers that are critical for effector functions through the Fc receptors.

Figure 1G:
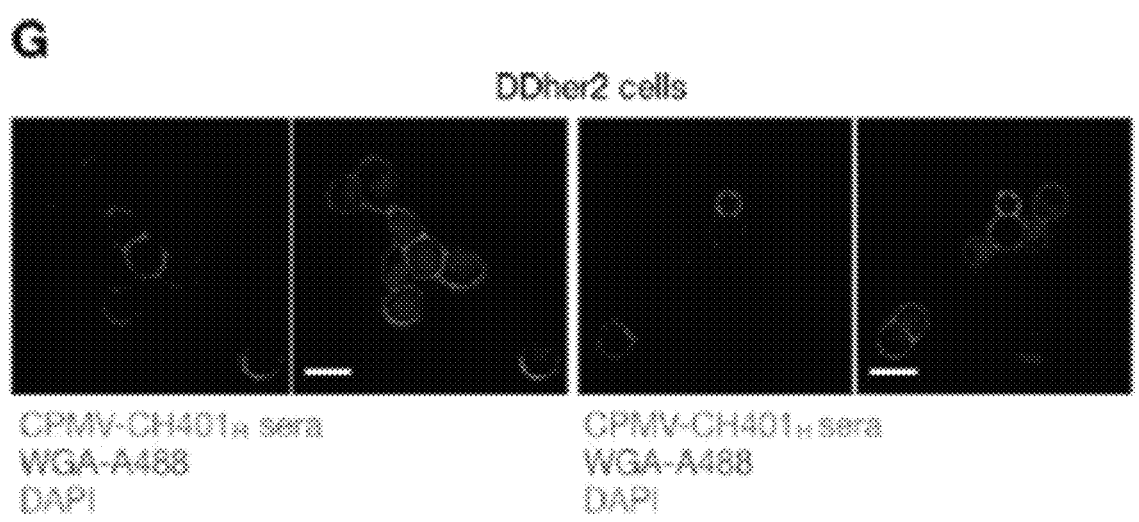
Figure 1H:
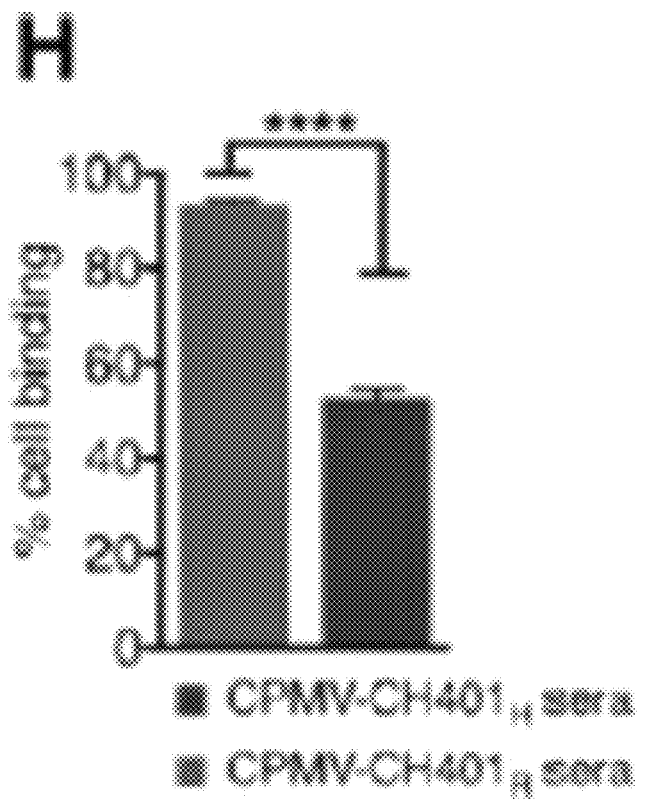

Next, we evaluated the ability of the mouse sera to recognize and bind cellular HER2 receptor on DDHER2 cells using confocal microscopy and flow cytometry (FIG. 1G,H). Confocal results show that both CPMV-CH401R sera and CPMV-CH401H sera recognize and bind to cellular HER2 receptors on DDHER2 cells (FIG. 1G). However, quantitative analysis using flow cytometry suggests that the former showed significantly higher binding over the latter (FIG. 1H). This is as expected because the DDHER2 cells express rat neu and highlights the need for species-specific formulations when developing and testing vaccines.

Figure 1I:
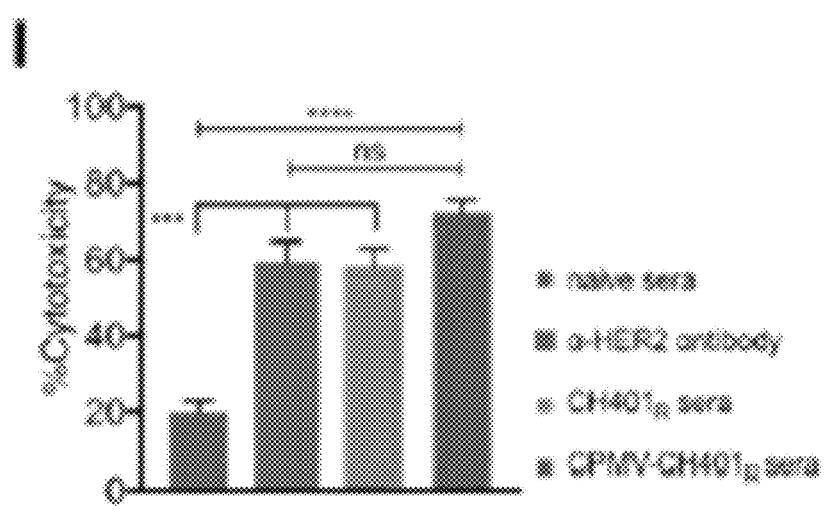

Following this, we evaluated the ability of CH401-specific antisera to neutralize HER2 expressing cancer cells using a MTT assay. We compared the CPMV-CH401R sera and CH401R sera with naive sera from nonimmunizedmice and with an anti-HER2 IgG to determine complement dependent cytotoxicity (CDC) against DDHER2 cells (FIG. 1I). We observed that under the tested conditions, sera from CPMV-CH401 or CH401 immunized mice showed significantly stronger cytotoxicity over naive sera. Thus, CH401-specific IgGs are able to recognize and bind to the cellular HER2 proteins and lead to complement mediated cytotoxicity similar to the effects exerted by the commercial anti-HER2 IgGs. While the CPMV-CH401 sera exerted elevated cytotoxicity over CH401 sera, the differences were not statistically significant under the tested in vitro conditions (low DDHER2 cell numbers and high sera concentrations) despite a significant difference in the anti-CH401 IgG titers between the two groups (FIG. 1E). To validate our results depicting enhanced immunogenicity of CPMVCH401 vaccine, we next compared the vaccine efficacy in vivo.

Testing Vaccine Efficacy in Primary and Metastatic Tumor Settings

Figure 2A:
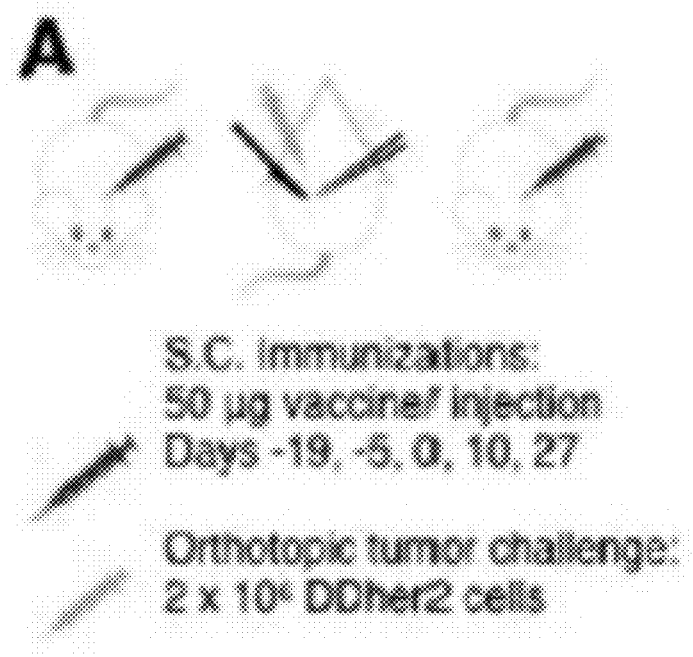
FIGS. 2(A-I) are graphical illustrations and images showing CPMV-CH401 vaccine efficacy in Balb/c mice: A) Female Balb/c mice were challenged DDHER2 cells orthotopically through surgical inoculations in mammary fat pads following two immunizations and followed by two more immunizations. B,C) Mice immunized with CPMV-CH401R (n=10) and CPMV-CH401H vaccines (n=9) showed significantly slower tumor progression as compared to nonimmunized mice (n=10) over a 60-day period. Data is plotted to day where n≥5 for each group. Statistical analysis between tumor volumes on days 20, 30, 40 and 55 was performed using ordinary one-way ANOVA using Tukey's multiple comparison (*p<0.0001, p<0.01, *p<0.05). D) Subcutaneous DDHER2 tumors were grafted on day 28 following immunization with CPMV-CH401R vaccine, free peptide, or PBS and received 3 more doses subsequently. E) Tumor progression was monitored and data was plotted to day where n≥5. F) Overall survival benefit between the immunized and control group was compared using Kaplan-Meier plot. Statistical analysis on the survival curves was performed using Log-rank (Mantel-Cox) test (*p<0.001). G,H) To model metastatic disease, DDHER2 cells were intravenously injected in mice immunized with CPMV-CH401R vaccine (n=5), free peptide (n=5) or PBS (n=3) (schematic is shown in G). Bioluminescence imaging on IVIS Spectrum Imaging system was used to monitor tumor progression in lungs over time (days 6, 9, 12) (H), and regions of interest (ROI) measurements were performed using the Living Image Software for a semi-quantitative analysis. Statistical analysis between treatment groups was performed using two-way ANOVA using Tukey's multiple comparison test (*p<0.001, *p<0.05).

Cancer vaccines have been generally classified as therapeutic vaccines and considered as adjuvant therapies post-surgical resection of the primary tumor. An effective cancer vaccine should be able to generate tumor antigen-specific cellular and/or humoral responses capable of recognizing residual or recurring cancer. With an anti-HER2 antibody response from the CPMV-based vaccines validated, we first compared the anti-tumor activity of the rat neu and human erbB2-specific vaccines in an orthotopic model usingD-DHER2 cells and Balb/c mice. Female Balb/c mice were immunized twice on day 0 and 14 with 50 μg of CPMV-CH401$_{R/H}$ or 21 μg of corresponding free peptides (the free peptide dose was normalized to the CPMV-CH401$_{R/H}$ dose). On day 19 after the first immunization, mice were challenged with an orthotopic inoculation of 2×10$^6$ DDHER2 cells in the inguinal mammary fat pads. Subsequently, two more doses of vaccines were administered 10 and 27 days following the tumor challenge (FIG. 2A). Control mice were challenged with tumors similarly but only received subcutaneous PBS injections as a mock immunization (FIG. 2A). Tumor growth was monitored daily once palpable tumors were observed.

Figure 2B:
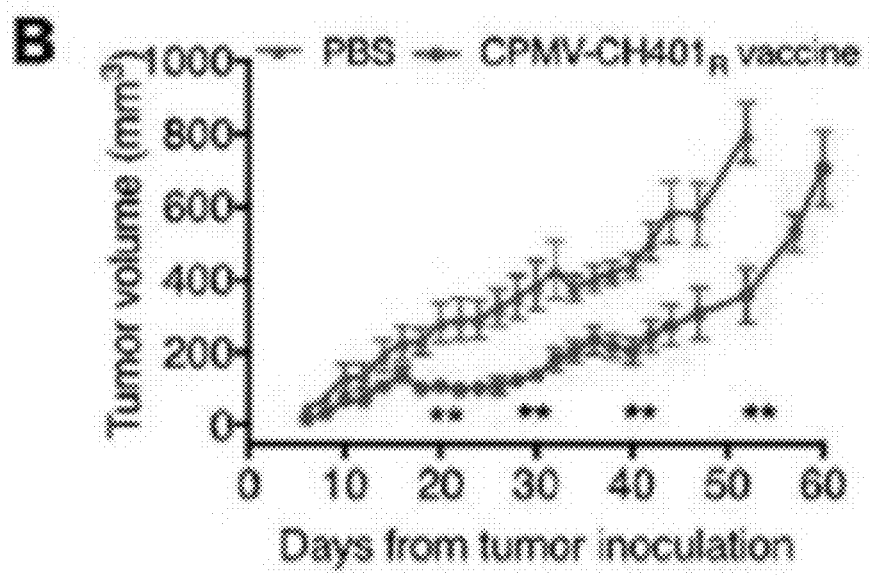
Figure 2C:
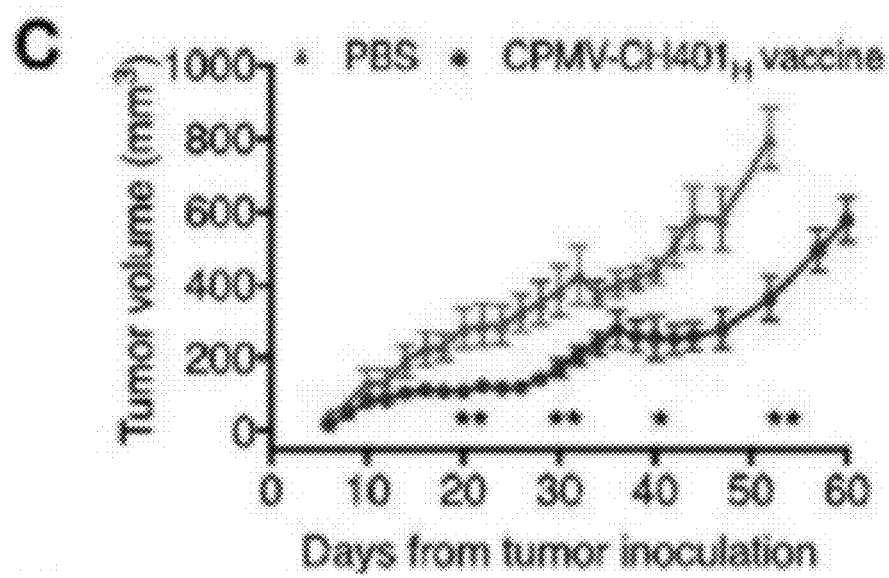

Compared to control mice, CPMV-CH401$_R$ and CPMV-CH401$_H$ vaccine immunized mice showed significantly slower tumor growth over 52 days of monitoring (FIG. 2B,C). It should be noted here that the tumor growth in immunized mice was impeded but never regressed. However, at day 52, the mean tumor volume of the PBS group was 1099 mm$^3$, while the CPMV-CH401$_R$ and CPMV-CH401$_H$ mean volumes were 448 mm$^3$ and 660mm$^3$, respectively. Also, throughout this period, the free peptide vaccine was outperformed by the CPMV-based vaccine from both groups and a larger proportion of CPMV-vaccine immunized mice demonstrated tumor volumes below 500 mm$^3$ compared to peptide-immunized mice on day 54 from tumor challenge. These results clearly underline the effectiveness of CPMV-CH401 vaccine in delaying orthotropic DDHER2 tumor growth. Our results also suggested that both rat and human vaccine formulations effectively slowed down the tumor growth. However, differences in the mean tumor volumes over the course of study could be correlated to the higher immunogenicity of the rat peptide as indicated by the elevated IgG titers from the CPMV-CH401R vaccine (FIG. 1). These results also corroborate previous studies suggesting higher efficacy of homologous vaccines in transplantable tumor models. Based on this, we used the CPMV-CH401R vaccine for all our subsequent experiments.

Figure 2D:
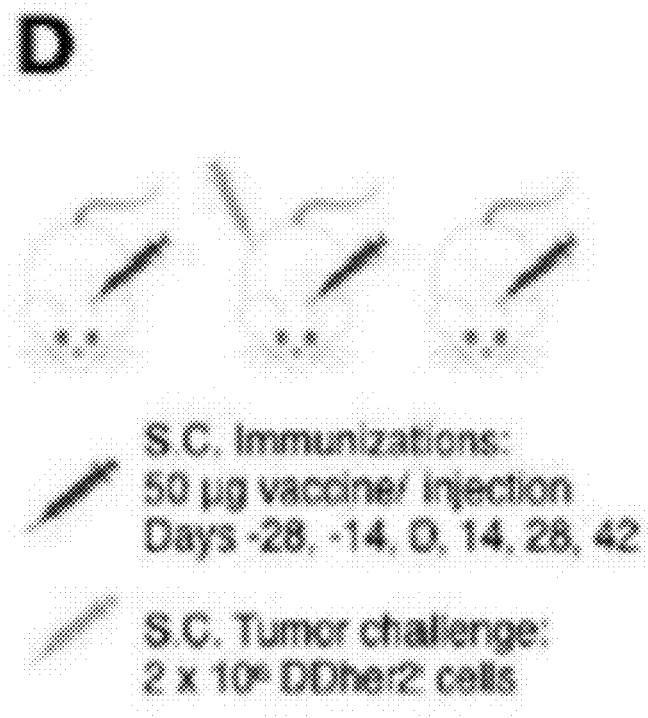
Figure 2E:
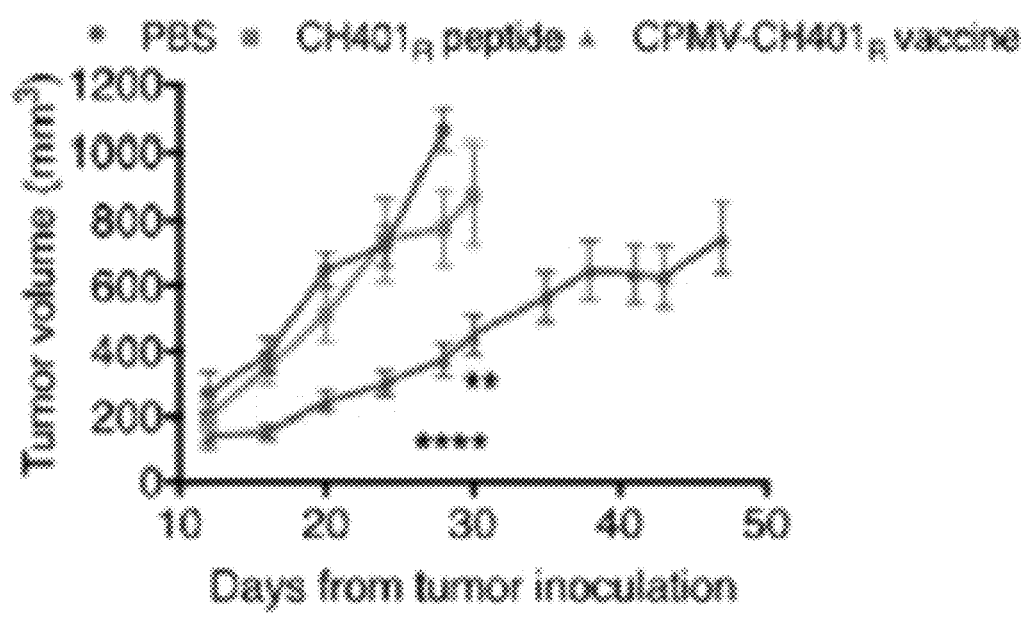
Figure 2F:
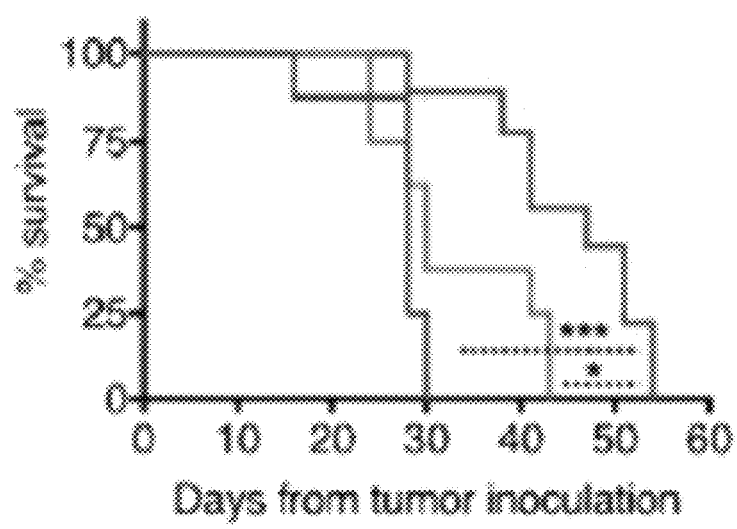

To further assess how robust the cancer vaccine is, we evaluated its efficacy in two additional settings using the DDHER2 cells: First, we evaluated the vaccine efficacy in a subcutaneous DDHER2 tumor model that showed a more aggressive growth pattern over the orthotropic model. Female Balb/c mice were immunized six times bi-weekly with CPMV-CH401$_R$ vaccine with two vaccinations occurring prior to tumor challenge, that is, the vaccine was given on 28 and 14 days prior to tumor challenge and bi-weekly vaccinations continued through day 42 post tumor challenge. The treatment group receiving the vaccine candidate CPMV-CH401R was compared with groups receiving free CH401R peptide or PBS (FIG. 2D). Tumors in PBS and free peptide groups grew rapidly and reached endpoint volumes around 30 days from inoculation, suggesting free peptide immunization without an adjuvant offers no protection against an aggressive HER2+ cancer. In stark contrast, mice immunized with CPMV-CH401$_R$ showed a significantly delayed tumor progression over a 50-day period (FIG. 2E), resulting in an overall survival advantage of 3 weeks over non-immunized mice (FIG. 2F).

Figure 2G:
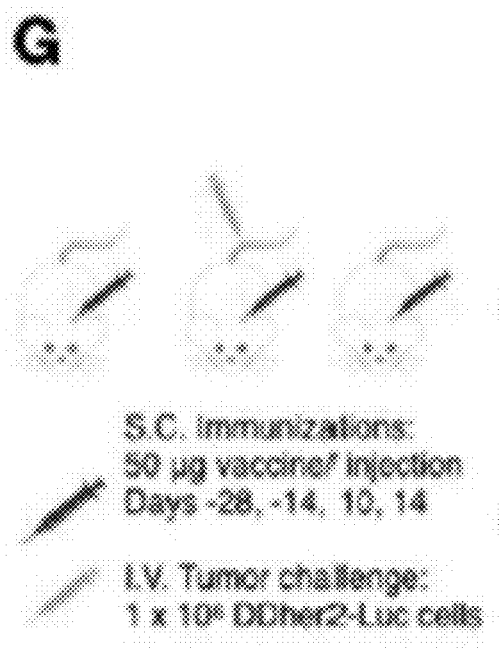
Figure 2H:
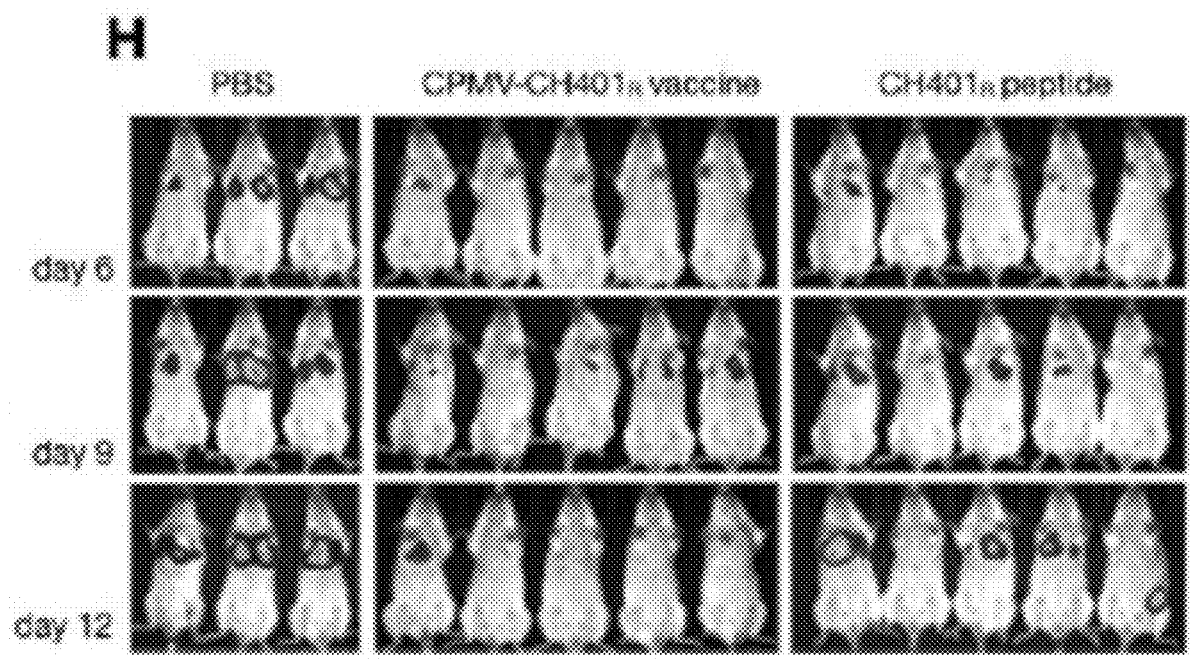
Figure 2I:
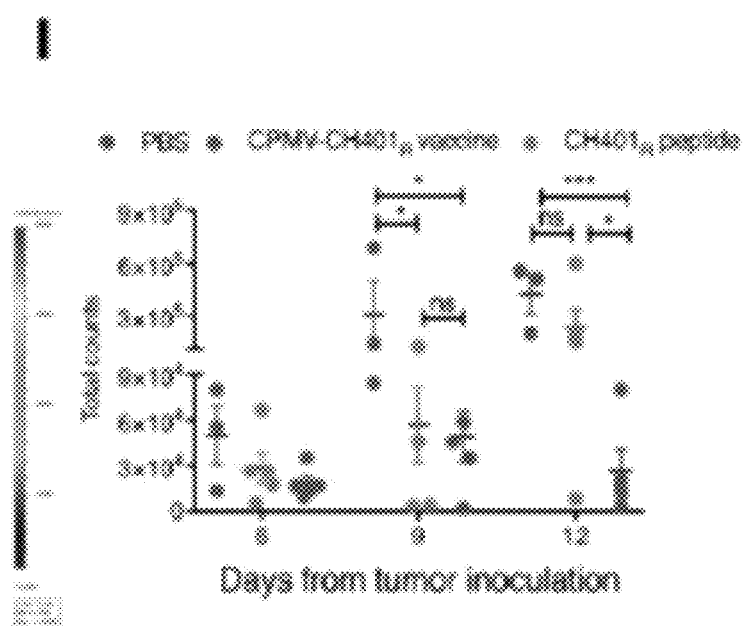

Metastasis is the main cause of mortality in breast cancer. HER2+ breast cancer in particular has an enhanced tendency to metastasize to distant organs including lungs, liver, bones, and brain. While primary tumors are subject to aggressive treatment regimens, metastases detection generally corresponds to an advanced stage of tumor, where the overall therapeutic goal is to prolong survival and generally, aggressive treatment is not pursued. To determine if HER2-reactive IgGs in sera could prevent lung metastasis, we challenged groups of control (n=3), CPMV-CH401$_R$ (n=5) or free CH401$_R$ immunized mice (n=5) with intravenous injections of bioluminescent DDHER2 cells (DDHER2-luc) obtained by transfecting DDHER2 cells with firefly luciferase using method described previously (FIG. 2G). Intravenously administered cancer cells rapidly home to lungs; disease burden in the lungs was monitored using bioluminescence imaging (FIG. 2H,I). Control mice started showing metastatic lesions in lungs as early as 6 days following the tumor challenge, and had significantly higher signal intensities over immunized mice. By day 12, intense bioluminescence signals were observed in all three PBS treated control mice; the mice showed clear signs of respiratory stress and were euthanized. Similarly, metastatic lesions were observed in CH401 peptide immunized mice starting on day 9; however, disease burden in four of these mice significantly increased and was comparable to the control mice by day 12 (FIG. 2I). In stark contrast, mice from the CPMV-CH401 treatment arm showed negligible bioluminescence signals that remained significantly lower than both control and CH401 groups up to day 12 (FIG. 2I). These results corroborate our observations from the orthotropic and subcutaneous tumor studies. Even the CPMV-CH401 immunized mice eventually developed lung metastases; however survival was prolonged for several days as mice were euthanized after day 16 (as opposed to day 12 for the PBS and free peptide control groups).

In a further set of studies, we evaluated the vaccine efficacy in immunized FVB/N mice that were challenged with orthotropic implants of HER2+ tumors derived from the transgenic MMTV-neuT strains. Female transgenic MMTV-neuT mice express neu under the transcriptional control of the mouse mammary tumor virus promoter. The females of this transgenic strain develop spontaneous tumors by 25-29 weeks of age. Tumors derived from transgenic females were collected and cut into small pieces of 2.5-3 mm; these were then surgically transplanted into the mammary fat pads of female FVB/N mice immunized with CPMV-CH401 vaccine, CH401 peptide, or PBS (n=9) (FIG. 3A). Tumor growth arising from cancerous tissues in this model was slower and showed more variation due to heterogeneity of tumor pieces. However, consistent with the aforementioned studies, tumor burden was reduced in CPMV-CH401 vaccinated animals. While non-vaccinated control mice (receiving PBS treatments) reached endpoint tumor volumes in 50-55 days post tumor implantation, immunized mice receiving CPMV-CH401 or free CH401 peptide showed distinct populations of responders versus non-responders where 55% of mice showed noticeably slower tumor growth as compared to non-immunized mice (FIG. 3B). Amongst this population of responders, however, there was nearly twofold difference in the tumor volumes of CPMV-CH401 immunized and free peptide administered mice (mean tumor volumes CPMV-CH401 responders versus CH401 responders for n≥3: 85.05 mm$^3$ versus 253.5 mm$^3$ (day 45), 151.6 mm$^3$ versus 372.6 mm$^3$ (day 49), 191.1 mm$^3$ versus 464.2 mm$^3$ (day 52), and 409.4 mm$^3$ versus 1002.43mm$^3$ (day 58)). Overall, immunized mice showed a survival benefit of nearly 40 days compared to non-immunized mice (FIG. 3B). We selected CH401 as epitope of choice based on its immunogenicity as reported earlier. It is apparent that in slow growing tumors, such as the orthotropic models discussed above, the peptide vaccine does show partial response in terms of slower tumor growth as compared to non-immunized mice. In conjugation with the CPMV carrier, however a more pronounced effect is obtained. A clearer and significant difference in the efficacy of VNP vaccine and free peptide is seen in the aggressively growing subcutaneous tumors, where CPMV-CH401 vaccine delayed tumor growth and enhanced survival.

Together, this set of studies demonstrates that the CPMV-CH401 vaccine candidate can effectively overcome the tolerance against the self-antigen and stimulate a strong humoral response capable of recognizing HER2 expressing tumor cells and slowing down growth of primary tumor as well as prevent metastatic spread.

Figure 4A:
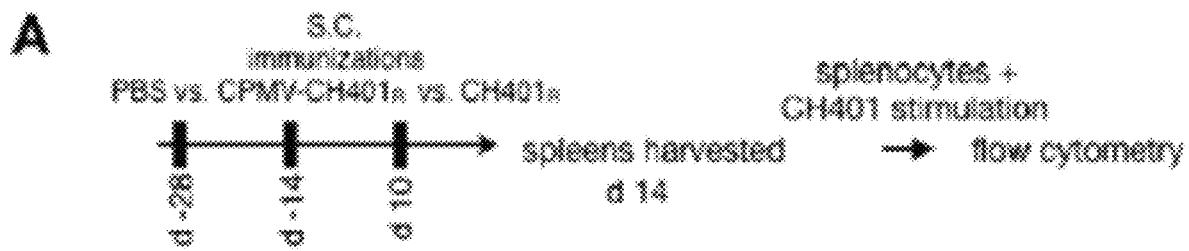
FIGS. 4(A-C) are graphical illustrations and cell cytometry images showing Flow cytometry analysis: A) Splenocytes isolated from immunized mice (n=5) were ex vivo stimulated with CH401 peptide and stained for intracellular IFN-γ. B and C) Cells were characterized as CD4+, CD8+ T cells, and effector memory CD4+, CD8+ T cells. Averages of triplicates with standard deviation are shown; statistical analysis was performed by one-way ANOVA using Tukey's multiple comparison test with, **p<0.005, *p<0.05.
Figure 4B:
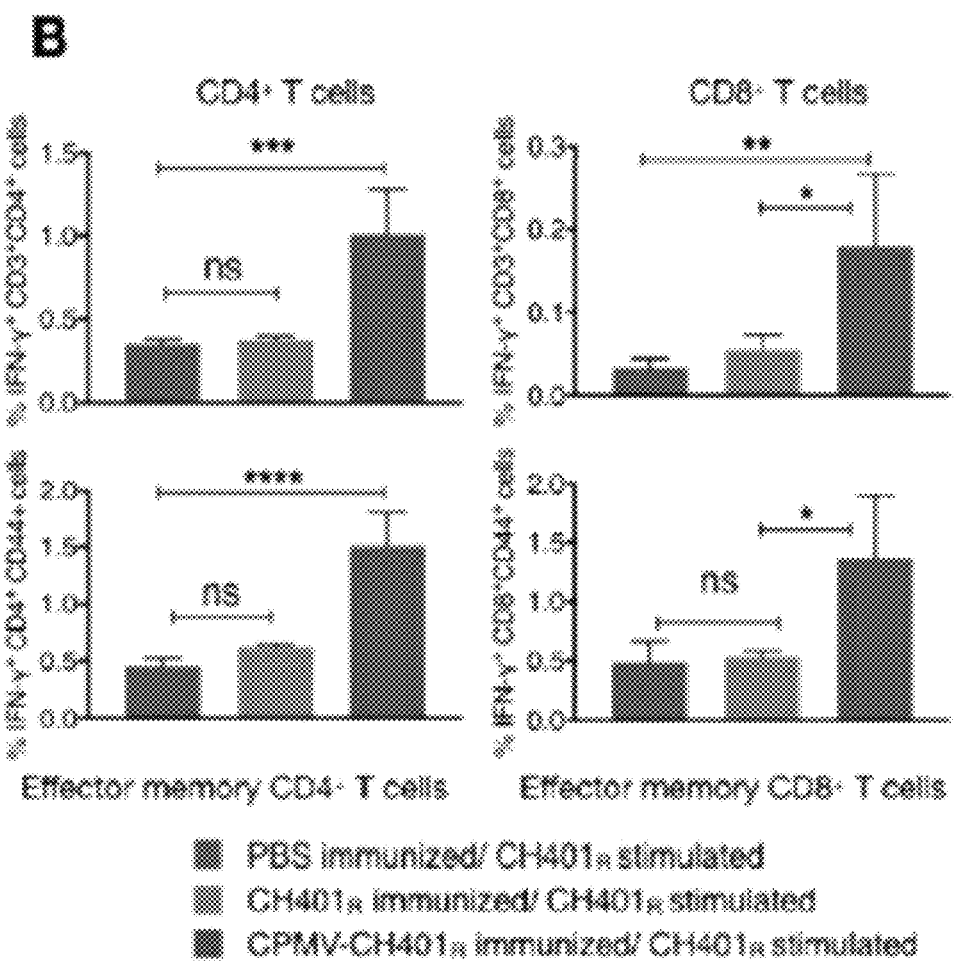
Figure 4C:
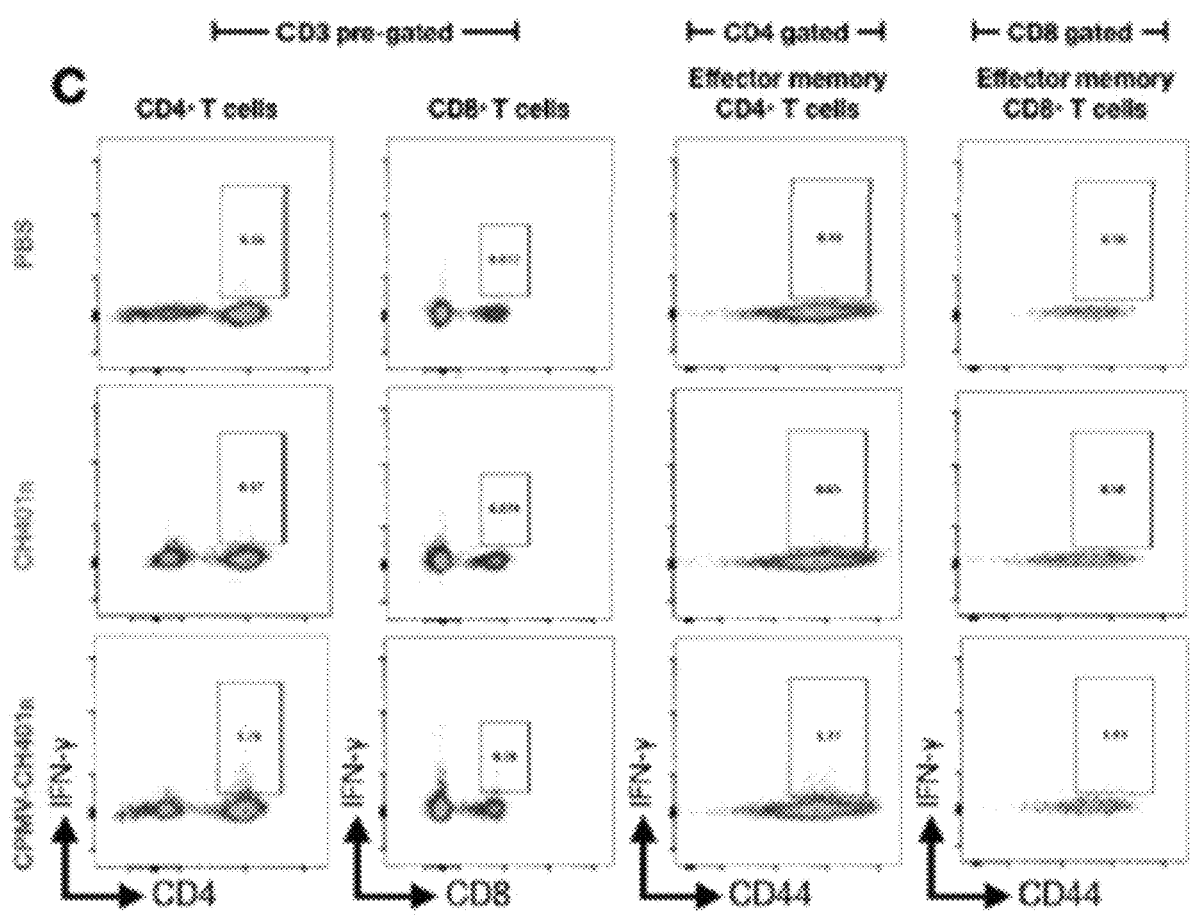

To gain an insight into the mechanism of the CPMV-CH401-induced anti-tumor immunity, we isolated splenocytes from immunized Balb/c mice following three immunizations and compared T cell populations following ex vivo stimulation with the CH401 peptide via intracellular IFN-γ staining (FIG. 4A). Cells were pre-gated with CD3 marker to distinguish CD4+ and CD8+ T cells subsets; subsequently CD4 and CD8 pregated cells were gated for CD44 to determine the fraction of effector:memory cell populations. We observed a significant increase in both IFN-γ+ CD4+ T cells and IFN-γ+ CD8+ T cells in the CPMV-CH401 vaccine group over peptide immunized and non-immunized groups (FIGS. 4B,C). While CD8+ T cells are the main players in the cytotoxic T cells (CTL) response, CD4+ T cells are critical for initiating and maintaining the CTL response against tumors. CD4+ T helper cells activate APCs and enhance expression of MHC and co-stimulatory molecules such as IL-12 that are crucial for an effective CTL response. CD4+ T helper cells also secrete IL-2 that recruits CTLs to tumor sites. IFN-γ production by CD4+ T helper cells also upregulate the expression of MHC molecules on tumor cells leading to enhanced CTL recognition. In addition to supporting the primary CTL activity, CD4+ T helper cells also play a role in generating and maintaining memory CD8+ T cells. Effective priming of CD4+ and CD8+ T cells is thus an important goal and was achieved using the CPMV-CH401 vaccine candidate with contributing effects from both carrier and epitope. The CH401 peptide has been reported to consist of both B-cell and T-helper cell epitopes while VNPs with their intrinsic immunogenicity serve as adjuvants and are considered activators of CD4+ T helper cell response. In addition, our results showed that the immunized group also boasted elevated fractions of IFN-γ+ CD4+ CD44+ and CD8+ CD44+ effector memory cells (FIGS. 4B,C), indicating the vaccine candidate primes durable anti-tumor immunity. Earlier studies have suggested that suppression of anti-HER2 Th1 response could promote tumorigenesis and is correlated with lack of response to neoadjuvant therapies. On the other hand, vaccines bearing potent CD4+ T helper epitopes have been shown to generate a more efficient CTL response against large doses of tumor cell challenges. Therefore, in addition to arresting tumor progression, a HER2 vaccine such as CPMV-CH401 could facilitate effectiveness of other anti-HER2 therapies by enhancing HER2-specific Th1 response.

Lastly, we tested the efficacy of combination immunotherapies. As noted earlier, while we noted significant delay in tumor and metastatic outgrowth upon vaccination with the CPMV-CH401 vaccine, disease elimination was not achieved. This highlights the aggressive nature of the DDHER2 tumor model, and also reflects on the poor prognoses in patients with HER2+ malignancies. Combinatorial approaches hold promise to boost the efficacy of cancer vaccines. Tumor antigen-specific antibodies, such as those generated by cancer vaccines can recognize and bind to transformed cells, but rely on the engagement of Fc-receptor expressing effector cells to kill the tumor cells through specific mechanisms including ADCC and phagocytosis. Stimulation of such effector cells could therefore enhance the therapeutic efficacy of the antibodies and vaccines. Several such approaches involving immunomodulators and cytokines are currently being evaluated to activate NK cells, dendritic cells, and macrophages. We hypothesized that the combination of the HER2 vaccine with an immunotherapy approach that attracts immune cells into the tumor bed may improve the efficacy of the vaccine. Toward this end, we and others have recently demonstrated the potential of plant VNP-based in situ vaccination. Here the immunostimulatory agent, the VNP, is administered directly into an identified tumor to modulate the local tumor microenvironment from immune-suppressive to immune-supportive, resulting in infiltration and activation of a broad spectrum of immune effector cells leading to local and systemic anti-tumor immune response. It was therefore reasoned that combining the CPMV-HER2 vaccine with the in situ vaccination approach (intratumoral administration of CPMV) could enhance the potency of the tumor antigen specific antibodies by the enriched milieu of effector cells in the tumor microenvironment. To test this hypothesis, female Balb/c mice received two immunizations with the CPMV-CH401 vaccine candidate; following tumor challenge with subcutaneous DDHER2 tumors in the flank, an additional two vaccinations were given (FIG. 5A). Starting at day 15 post-tumor inoculation, that is, when tumors were established, in situ vaccination was initiated and CPMV (100 μg of CPMV in 20 μL PBS per each tumor) was administered by intratumoral (I.T.) injections on a weekly basis for 4 weeks. Tumor growth was measured and results were compared with control mice (non-immunized, no I.T. CPMV), CPMV vaccine+PBS I.T. group, PBS S.C.+CPMV I.T., and CPMV-CH401 vaccine S.C.+CPMV I.T. groups. Our results indicated that mice receiving intratumoral CPMV injections alone or CPMV-CH401 vaccine alone showed comparably inhibited tumor growth patterns (FIG. 5B), with a survival period of 44 days as compared to the rapid growth of untreated tumors with an overall survival of 28 days (FIG. 5C). Most importantly, the combination of these two approaches leads to a greater survival benefit than either single agent. Mice from the combination treatment arm showed a significantly slower tumor growth with average tumor volumes that were half of control mice by day 30 and an overall survival of 56 days. (FIG. 5C).

Together, these results illustrate that plant VNPs with their inherent immunostimulatory nature are excellent carriers of tumor antigens and can lead to a strong and sustained anti-tumor immune response. These biocompatible carriers obviate the need for additional adjuvants.

In conclusion, our studies validate the potency and potential of CPMV-based cancer vaccines. In this study, we have demonstrated the potency of plant viral nanoparticle CPMV-based HER2 vaccine to induce a strong and sustained anti-HER2 immune response. The efficacy of this vaccine to regress tumor growth and prolong survival is then illustrated using primary and metastatic mice models of HER2+ cancer. Given the simplicity of design and manufacturing, such therapeutic vaccines based on the biocompatible CPMV platform technology could offer cost effective and potent alternatives to current adjuvant therapies.

What is claimed is:

1. An anti-cancer particle composition comprising an icosahedral-shaped plant virus or virus-like particle linked to a HER2 antigen, wherein the HER2 antigen comprises all or a portion of the amino acid sequence located between position 163 and 182 of human HER2 protein.

2. The anti-cancer composition of claim 1, wherein the plant virus or plant virus-like particle is of the Secoaviridae family.

3. The anti-cancer particle composition of claim 1, wherein the plant virus or plant virus-like particle is of the genus *Comovirus*.

4. The anti-cancer particle composition of claim 1, wherein the plant virus or plant virus-like particle is a cowpea mosaic virus (CPMV) or CPMV virus-like particle.

5. The anti-cancer particle composition of claim 1, wherein the HER2 antigen comprises a B-cell and a T-cell epitope from the extracellular domain of HER2.

6. The anti-cancer particle composition of claim 1, wherein the HER2 antigen comprises a peptide having an amino acid sequence selected from YQDTILWKDIFHKNNQLALT (SEQ ID NO:13) and YQDMVLWKDVFRKNNQLAPV (SEQ ID NO:14).

7. The anti-cancer particle composition of claim 6, wherein the HER2 antigen comprises a cysteine terminated HER2 peptide with an intervening flexible linker.

8. The anti-cancer particle composition of claim 7, wherein the HER2 antigen comprises a peptide having an amino acid sequence selected from YQDTILWKDIFHKNNQLALT-GPSL-C (SEQ ID NO:15) and YQDMVLWKDVFRKNNQLAPV-GPSL-C (SEQ ID NO:16).

9. The anti-cancer particle composition of claim 1, further comprising a pharmaceutically acceptable carrier.

10. A method of treating or decreasing the risk of developing a HER2-expressing cancer in a subject, by comprising administering to a subject in need thereof an effective amount of an anti-cancer particle composition comprising an icosahedral-shaped plant virus or virus-like particle linked to a HER2 antigen, wherein the HER2 antigen comprises a B-cell and a T-cell epitope from the extracellular domain of HER2 epitope homologous to the species of subject being treated.

11. The method of claim 10, wherein the plant virus or plant virus-like particle is of the Secoaviridae family.

12. The method of claim 10, wherein the plant virus or plant virus-like particle is of the genus *Comovirus*.

13. The method of claim 10, wherein the plant virus or plant virus-like particle is a cowpea mosaic virus (CPMV) or virus-like particle.

14. The method of claim 10, wherein the HER2 antigen comprises all or a portion of the amino acid sequence located between position 163 and 182 of human HER2 protein.

15. The method of claim 10, wherein the HER2 antigen comprises a peptide having an amino acid sequence selected from YQDTILWKDIFHKNNQLALT (SEQ ID NO:13) and YQDMVLWKDVFRKNNQLAPV (SEQ ID NO:14).

16. The method of claim 10, wherein the HER2 antigen comprises a cysteine terminated HER2 peptide with an intervening flexible linker.

17. The method of claim 10, wherein the HER2 antigen comprises a peptide having an amino acid sequence selected from YQDTILWKDIFHKNNQLALT-GPSL-C (SEQ ID NO:15) and YQDMVLWKDVFRKNNQLAPV-GPSL-C (SEQ ID NO:16).

18. The method of claim 10, wherein the HER2-expressing cancer is selected from breast, ovary, recto-colon, lung, prostate, stomach, pancreatic, and biliary cancer.

19. The method of claim 10, wherein the HER2-expressing cancer is HER2+ breast cancer.

* * * * *